(12) United States Patent
Gahroosi et al.

(10) Patent No.: US 11,644,451 B2
(45) Date of Patent: May 9, 2023

(54) SYSTEMS AND METHODS FOR DETECTING A SENSING EVENT IN A STREAM OF CHEMICAL SENSOR MEASUREMENT DATA

(71) Applicant: Stratuscent Inc., Montreal (CA)

(72) Inventors: Amir Bahador Gahroosi, Montreal (CA); Neven Maric, Montreal (CA); Ashok Prabhu Masilamani, Montreal (CA); Mojtaba Khomami Abadi, Montreal (CA)

(73) Assignee: Stratuscent, Inc., Montreal (CA)

( * ) Notice: Subject to any disclaimer, the term of this patent is extended or adjusted under 35 U.S.C. 154(b) by 123 days.

(21) Appl. No.: 17/196,862

(22) Filed: Mar. 9, 2021

(65) Prior Publication Data
US 2021/0285923 A1    Sep. 16, 2021

Related U.S. Application Data

(60) Provisional application No. 62/987,607, filed on Mar. 10, 2020.

(51) Int. Cl.
*G01N 33/00* (2006.01)
*G06N 20/00* (2019.01)

(52) U.S. Cl.
CPC ..... *G01N 33/0062* (2013.01); *G01N 33/0075* (2013.01); *G06N 20/00* (2019.01)

(58) Field of Classification Search
CPC .......... G01N 33/0062; G01N 33/0075; G01N 33/0009; G01N 33/0067; G01N 33/0073; G01N 2033/0068
See application file for complete search history.

(56) References Cited

U.S. PATENT DOCUMENTS

| 2004/0219691 | A1 | 11/2004 | Shartle et al. |
| 2006/0073483 | A1* | 4/2006 | White ............... C12Q 1/6825 435/6.1 |
| 2017/0069010 | A1* | 3/2017 | Amin ................. G01N 33/0031 |
| 2020/0400631 | A1* | 12/2020 | Gao ....................... G01N 27/12 |
| 2021/0278387 | A1* | 9/2021 | Bistany .................. F24F 11/88 |

FOREIGN PATENT DOCUMENTS

| WO | WO 00/26638 A1 | 5/2000 |
| WO | WO 2013/098563 A1 | 7/2013 |

OTHER PUBLICATIONS

International Search Report and Written Opinion dated Jul. 20, 2021 in connection with International Application No. PCT/IB2021/000129.

* cited by examiner

*Primary Examiner* — Manuel L Barbee
(74) *Attorney, Agent, or Firm* — Pierce Atwood, LLP

(57) ABSTRACT

Described herein is a chemical sensing system that can be deployed in an environment and automatically monitor the environment. The chemical sensing system includes one or more chemical sensing units with sensing elements that sense chemicals in the environment. The chemical sensing system analyzes measured values output by the sensing elements to identify patterns indicative of events. After identifying an event, the chemical sensing system may generate an inference about the environment using measured values output by the sensing elements during the event.

21 Claims, 13 Drawing Sheets

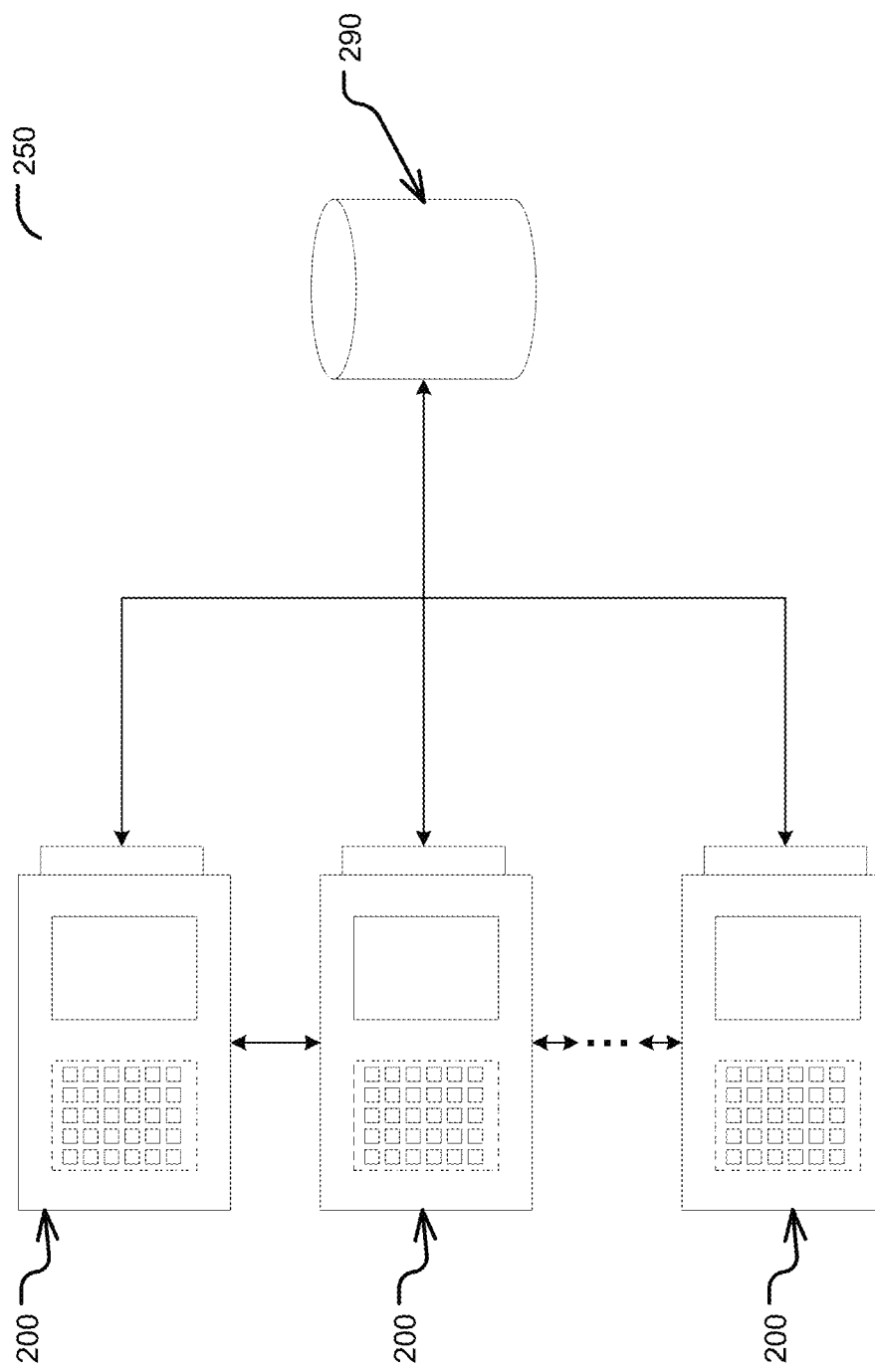

SYSTEMS AND METHODS FOR DETECTING A SENSING EVENT IN A STREAM OF CHEMICAL SENSOR MEASUREMENT DATA

RELATED APPLICATIONS

This application claims priority under 35 U.S.C. § 119(e) to U.S. Provisional Application 62/987,607 entitled, "PATTERN ORIENTED TRIGGER SCENE AND INSTANT CONTINUOUS INFERENCE SYSTEM," filed Mar. 10, 2020, the entire contents of which is incorporated by reference herein.

FIELD

This application relates generally to techniques that allow a chemical sensing system to automatically detect a sensing event occurring in an environment based on a stream of measurement data collected by sensing elements of the chemical sensing system. In response to detecting the sensing event, the chemical sensing system may initiate generation of an inference for the detected sensing event.

BACKGROUND

Different chemicals may be present in an environment based on characteristics of the environment including activities that are taking place in the environment. For example, a space in a home may include multiple different chemicals that are present in the air in the room. Chemicals in the room may change based on physical processes occurring in the space. For example, the chemicals in a kitchen may change when someone is cooking food in the kitchen. In another example, an odor in a bathroom may change based on what is taking place in the bathroom. Humans and other species have chemical receptors that allow them to perceive chemicals in an environment. For example, a sense of smell may allow them to perceive chemicals through scent.

The chemical receptors of a species have mechanisms that increase the chance of survival for the species in its environment. For example, in order to enable the species to (i) find food or detect prey, (ii) find mates for reproduction, (iii) detect threats like predators, water, and or fire associated with scent. For example, in humans, there are approximately 400 genomes that produce different types of neural receptors that reside in the human nostril (as well as other parts of the body) to detect odors, smells and chemicals in the environment. The receptors, as exposed to certain chemicals to which they are sensitive, make bonds with the chemicals and produce electro-chemical signals. Different receptors may respond to the same chemical differently and due to (i) the diversity in the receptors, (ii) topological distribution of the receptors and (iii) slight differences in the replication of the same type of receptor, the collective electro-chemical outputs of the odor receptors contain information content of the chemical composition of the species' environment, that the odor receptors are evolved to capture.

SUMMARY

Aspects of the present application relate to a chemical sensing system configured to determine information about an environment within which the chemical sensing system is located. The chemical sensing system may be deployed in an environment and monitor the environment. The chemical sensing system includes one or more chemical sensing units with sensing elements that sense chemicals in the environment. The chemical sensing system analyzes measured values output by the sensing elements to identify patterns indicative of events. After identifying an event, the chemical sensing system may generate an inference about chemical characteristics of the environment using measured values output by the sensing elements during the occurrence of the event.

According to some embodiments, a chemical sensing system is provided. The chemical sensing system comprises: a chemical sensing unit comprising a plurality of sensing elements, each of the plurality of sensing elements being configured to sense a respective one or more chemicals in an environment of the chemical sensing system; a computer processor; and a non-transitory computer-readable storage medium storing instructions that, when executed by the computer processor, cause the computer processor to perform a method comprising: receiving, from the chemical sensing unit, a first plurality of measurements comprising measured values output by the plurality of sensing elements at a plurality of points in a period of time; identifying, using the first plurality of measurements, a first timepoint corresponding to an occurrence of an event at least in part by analyzing the measured values output by the plurality of sensing elements to identify a pattern indicative of the occurrence of the event; and after identifying the occurrence of the event, generating an inference about chemical characteristics of the environment of the chemical sensing system using a second plurality of measurements, the second plurality of measurements comprising measured values output by the plurality of sensing elements after the first timepoint.

According to some embodiments, a method performed by a chemical sensing system to determine information about an environment of the chemical sensing system is provided. The method comprises: sensing, by a plurality of sensing elements of a chemical sensing unit, one or more chemicals in the environment; using a computer processor to perform: receiving, from the chemical sensing unit, a first plurality of measurements comprising measured values output by the plurality of sensing elements at a plurality of points in time; identifying, using the first plurality of measurements, a first timepoint corresponding to an occurrence of an event at least in part by analyzing the measured values output by the plurality of sensing elements to identify a pattern indicative of the occurrence of the event; and after identifying the occurrence of the event, generating an inference about chemical characteristics of the environment of the chemical sensing system using a second plurality of measurements, the second plurality of measurements comprising measured values output by the plurality of sensing elements after the first timepoint.

According to some embodiments, a system for determining information about an environment using measurement information obtained by a chemical sensing unit comprising a plurality of sensing elements is provided. The system comprises: a computer processor; and a non-transitory computer-readable storage medium storing instructions that, when executed by the computer processor, cause the computer processor to perform a method comprising: receiving, from the chemical sensing unit, a first plurality of measurements comprising measured values output by the plurality of sensing elements at a plurality of points in a period of time; identifying, using the first plurality of measurements, a first timepoint corresponding to an occurrence of an event at least in part by analyzing the measured values output by the plurality of sensing elements to identify a pattern indicative of the occurrence of the event; and after identifying the occurrence of the event, generating an inference about chemical characteristics of the environment of the chemical sensing system using a second plurality of measurements, the second plurality of measurements comprising measured values output by the plurality of sensing elements after the first timepoint.

The foregoing summary is provided by way of illustration and is not intended to be limiting. It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

FIGS. 2A-2C illustrate components of an example chemical sensing unit, according to some embodiments of the technology described herein.

DETAILED DESCRIPTION

Figure 1:
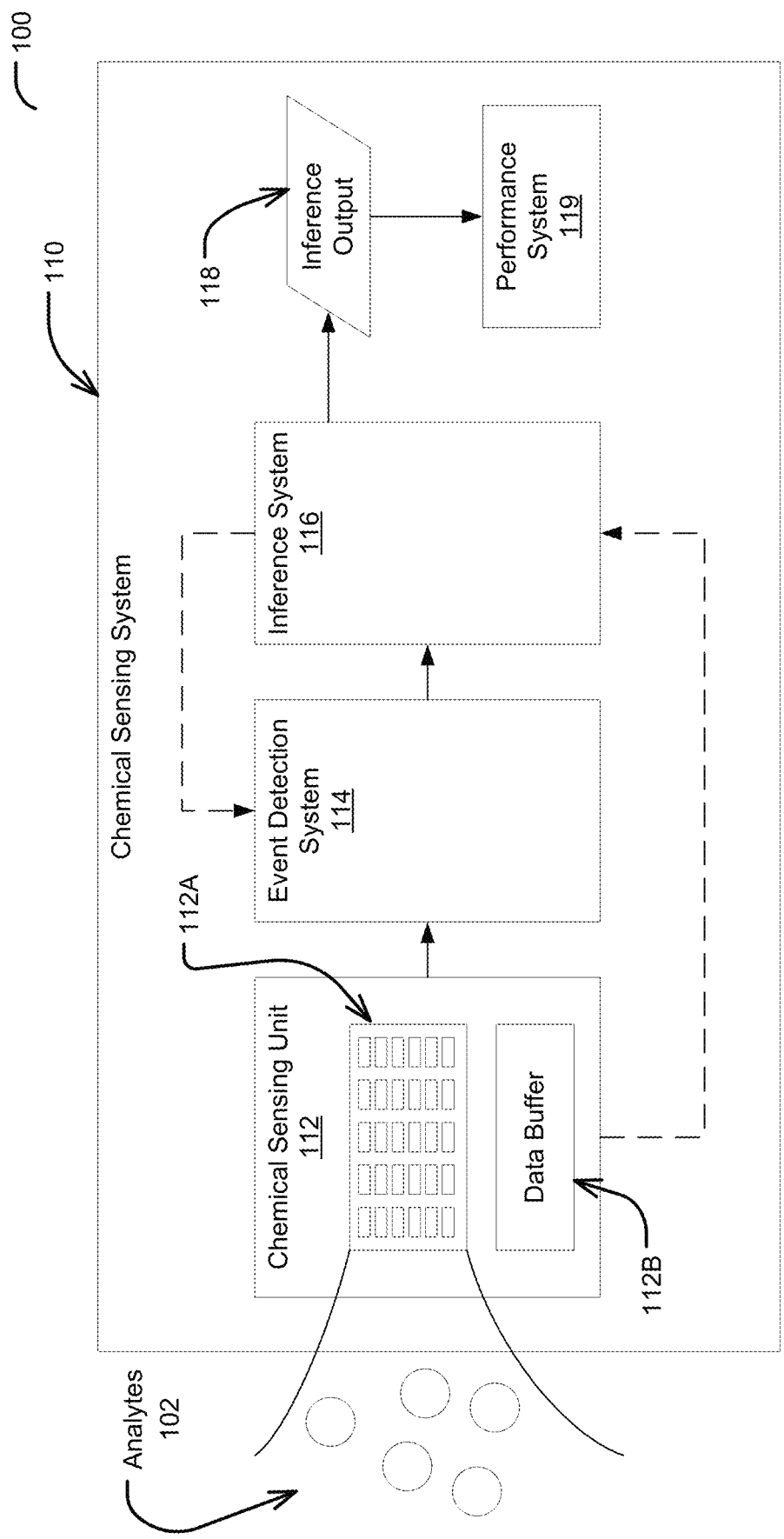
FIG. 1 illustrates an example environment in which some embodiments of the technology described herein may be implemented.

A chemical sensing system may be used to determine information about an environment by analyzing chemicals in the environment. The chemical sensing system may analyze the chemicals using sensing elements. A sensing element (also referred to as a "sensor") may interact with one or more chemicals in the environment and generate a response. For example, a sensing element may undergo a chemical interaction in which molecules of the sensing element bond with those of the chemical(s). The sensing element may generate a measurement (e.g., a voltage signal) based on the interaction. The chemical sensing system may use measurements output by the sensing elements to determine information about the environment. As an illustrative example, the chemical sensing system may use the measurements to identify one or more scents or odors in the environment.

Some conventional chemical sensing systems rely on manual user action to initiate a process for determining information about the environment, such as generating an inference about one or more chemical characteristics of the environment. Such chemical systems that rely on manual user action are unable to operate autonomously. Other conventional chemical sensing systems may detect a change in a signal output by a sensing unit to initiate an inference generation process. However, such chemical sensing systems tend to be highly prone to noise and thus are susceptible to making false detections. The inventors have thus recognized that conventional chemical sensing systems are typically limited in their ability to operate in an environment continuously and autonomously, which limits practical applications in which the chemical sensing system may be used. For example, in the context of scent detection, changes in scent may occur gradually over a period of time as a result of chemical processes that release compounds into an environment. In this context, if a user wants to be alerted when a particular scent or odor (e.g., due to growth of mold) is present in an environment, use of a chemical sensing system that requires user action to identify the scent or odor may not be practical for automatic detection of the particular scent or odor of interest.

Accordingly, the inventors have developed a chemical sensing system that reliably detects an event of interest in an environment without requiring user input, and determines information about the environment based on the detection. The chemical sensing system may thus be deployed for continuous autonomous operation in an environment. The chemical system may, for example, be used for scent monitoring in an environment as it may autonomously monitor the environment to detect changes in scents present in the environment, and identify scents in response to the detected changes. For example, based on detecting the change in scent, the chemical sensing system may identify one or more new scents introduced into the environment (e.g., as a result of growth of mold). The chemical sensing system may provide a notification to a user of the detected change and/or automatically trigger an action. For example, the chemical sensing system may be used as part of a mold detection system in which the chemical sensing system's identification of a scent associated with growth of mold is used to trigger a release of fungicide in the environment.

According to some embodiments, a chemical sensing system configured to automatically detect occurrence of an event is provided. The chemical sensing system may generate an inference about the environment based on detection of the occurrence of the event. An "event" may refer to a changed state of the environment for which the chemical sensing system is to generate an inference. For example, an event may be an introduction of one or more chemicals (e.g., organic compounds) into the environment resulting in a scent being introduced into the environment. In this example, the chemical sensing system may generate an inference that identifies the scent.

In some embodiments, the chemical sensing system includes a chemical sensing unit that houses multiple sensing elements. Each of the sensing elements may be configured to sense a respective one or more chemicals or one or more classes of chemicals. The sensing elements may generate measurements comprising measured values (e.g., voltage signal values) obtained at points in a period of time. The chemical sensing system may identify, using the measurements, a timepoint corresponding to an occurrence of an event by analyzing the measurements to identify a pattern (e.g., in voltage values) indicative of the occurrence of the event. For example, the timepoint may correspond to a start of the event. After identifying the occurrence of the event, the chemical sensing system may generate an inference about one or more chemical characteristics of the environment using measurements after the timepoint corresponding to the occurrence of the event. For example, the chemical sensing system may, in response to identifying the occurrence of the event: (1) generate a set of features; and (2) provide the set of features as input to a machine learning model to obtain an output (e.g., indicating a concentration of one or more analytes, an identified scent, and/or other information).

A chemical characteristic of an environment may refer to any characteristic of the environment related to one or more chemicals in the environment. Examples of a chemical characteristic of an environment include a scent in the environment, a concentration of one or more chemicals in the environment, pH, humidity, presence of one or more chemicals, temperature, toxicity, flammability, acidity, and/or another chemical characteristic.

In some embodiments, the chemical sensing system may be configured to analyze measurements output by the sensing elements to identify a pattern indicative of the occurrence of an event by generating a set of features using the measurements, and providing the set of features as input to a machine learning model to obtain an output. The output may indicate whether the set of features is indicative of the occurrence of an event. For example, the machine learning model may be trained to identify one or more patterns corresponding to an occurrence of an event. The chemical sensing system may be configured to provide information (e.g., measurements and/or a set of features) to an inference module when an event is detected.

In some embodiments, the chemical sensing system may be configured to analyze measurements output by the sensing elements to identify a pattern indicative of the occurrence of an event by: (1) determining a reference state; and (2) identifying a change from the reference state indicative of the occurrence of the event. A reference state may refer to a state of the environment at a time when an event has not occurred. For example, in the context of scent detection, a reference state may be the state of the environment prior to introduction of chemical(s) in the environment that result in a new scent. The chemical sensing system may be configured to generate an indication of the reference state using measurements output by the sensing elements. For example, the system may use a machine learning model (e.g., a neural network) to generate the indication of the reference state. The chemical sensing system may be configured to use the indication of the reference state to identify a change from the reference state in the environment.

Some embodiments of the chemical sensing system described herein may be applied in the context of various continuous monitoring systems. For example, some embodiments may be used as part of a smart cooking assistant. A recipe may be described as a sequence of stages such as: heating, adding ingredients, stirring, flipping, reaching an optimal cooking point (e.g., crispy and/or dry). Each stage in this sequence may have a unique and characteristic aroma that can be wholesomely captured by a chemical sensing system (e.g., integrated into a cooking range) in a continuous manner throughout the cooking process. As the cooking transitions through the sequence, stages the chemical sensing system may identify events corresponding to transitions occurring (e.g., in scent). The chemical sensing system may predict the stages of each recipe and automatically guide the cooking range to the desired doneness or extra crispiness of the recipe based on user preference.

In another example, some embodiments may be implemented as part of a smart deodorant dispenser. A deodorizer may be a specially formulated spray (e.g., mounted in restrooms, public spaces, hotels etc.) that can neutralize other odors in an environment. Conventionally they are programmed to be sprayed based on a timer which can lead to wastage of the deodorizer solution when, for example, a bathroom in which the deodorizer is installed has not been used. A smart deodorizer incorporating a chemical sensing system of some embodiments may continuously monitor the scent(s) of the environment and trigger the deodorizer when an odor meets a threshold.

In another example, some embodiments may be implemented in a produce spoilage detection system (e.g., for usage inside a truck or shipping container). Produce may get spoiled in storage or transportation systems due to fungal infections. Fungi may produce characteristic spores and volatile organic compounds (VOCs) that may, in combination, represent a state of the spoilage. A chemical sensing system of some embodiments may be configured to continuously detect chemical signatures that represent early stages of fungal growth (e.g., that attack fruits and vegetables). When the chemical sensing system detects a state representing fungal growth in the environment, fungicide may be dispensed into the environment to counteract the fungal growth.

FIG. 1 illustrates an example environment 100 in which some embodiments of the technology described herein may be implemented. As shown in FIG. 1, the environment 100 includes multiple analytes 102 and a chemical sensing system 110 configured to sense the analytes 102. An analyte may be a chemical, or a combination of multiple chemicals. For example, the analyte may be one or more chemicals that the chemical sensing system 110 may be configured to sense. As an illustrative example, an analyte may be nitrogen, oxygen, carbon dioxide, methane, and/or a combination thereof. The chemical sensing system 110 may be configured to generate an inference output 118 about chemical characteristic(s) of the environment 100 based on sensing the analytes 102.

As shown in FIG. 1, the chemical sensing system 110 includes a chemical sensing unit 112, an event detection system 114, and an inference system 116.

In some embodiments, the chemical sensing unit 112 is configured to sense analytes 102 in the environment 100. As shown in the example of FIG. 1, the chemical sensing unit 112 includes a set of sensing elements 112A. The chemical sensing unit 112 may be configured to sample analytes 102 from the environment 100 and expose the analytes 102 to the sensing elements. For example, the chemical sensing unit 112 may include a suction mechanism (e.g., a vacuum) that the chemical sensing unit 112 uses to intake (e.g., suction) the analytes 102 from the environment 100. The chemical sensing unit 112 may pump the analytes 102 and expose the analytes 102 to the sensing elements 112A.

In some embodiments, the sensing elements 112A may be arranged in an array as illustrated in FIG. 1. Each of the sensing elements 112A may be configured to sense one or more chemicals in the environment 100. For example, a sensing element may sense molecules of one or more chemicals. In some embodiments, a sensing element may be configured to sense a class of chemicals. For example, the sensing element may sense a functional chemistry group of interest (e.g., related to an odor of interest).

In some embodiments, the sensing elements 112A may be positioned proximate (e.g., over) a surface that is exposed to analytes. For example, the sensing elements 112A may be seated on a substrate enclosed within a volume (also referred to as a "headspace"). The sensing elements 112A may be exposed to analytes 102 sampled by the chemical sensing unit 112. In some embodiments, a sensing element may be configured to undergo a chemical reaction with one or more analytes that the sensing element is exposed to. For example, the sensing element may form weak intermolecular bonds with molecules of chemical(s) resulting in changes in chemo-physical characteristics of the sensing element's material. The sensing element may be configured to output a measurement indicative of a change in its chemo-physical characteristics. In some embodiments, the sensing element may be configured to output one or more measured values. For example, the sensing element may output a voltage signal indicating the change in chemo-physical characteristics of the chemical sensing element's material.

In some embodiments, the sensing elements 112A may be configured to continuously sense analytes 102 in the environment 100. The chemical sensing unit 112 may be configured to continuously sample analytes 102 from the environment 100 and expose the analytes 102 to the sensing elements 112A. For example, the chemical sensing unit 112 may periodically sample the analytes every 1 second, 5 seconds, 10 seconds, 1 minute, 5 minutes, 10 minutes, 30 minutes, 1 hour, 2 hours, 12 hours, 24 hours, and/or other suitable frequency. In some embodiments, the chemical sensing unit 112 may be configured to leave the sensing elements 112A exposed to the environment 100 such that the set of sensing elements 112A is always exposed to the analytes 102 in the environment 100.

In some embodiments, the sensing elements 112A may be configured to continuously output measured values (e.g., of a voltage signal) determined from the sensing. In some embodiments, the set of sensing elements 112A may be configured to output the measured values periodically. For example, the set of sensing elements 112A may: (1) perform a measurement; and (2) output measured values every 1 second, 5 seconds, 10 seconds, 1 minute, 5 minutes, 10 minutes, 30 minutes, 1 hour, 2 hours, 12 hours, 24 hours, and/or other suitable frequency.

As shown in FIG. 1, the chemical sensing unit 112 includes a data buffer 112B. The data buffer 112B may be configured to store values output by the sensing elements 112A. In some embodiments, the data buffer 112B may be memory configured to store measured values output by the sensing elements 112A. For example, voltage signal values output by the sensing elements 112A may be stored in the data buffer 112B for subsequent usage (e.g., for event detection and/or inference). In some embodiments, the data buffer 112B may be a region of physical memory storage. For example, the data buffer 112B may be a portion of random access memory (RAM), a hard disk drive, a solid state drive, or other type of physical memory storage.

In some embodiments, the data buffer 112B may be configured to temporarily store measured values output by the set of sensing elements 112A. In some embodiments, the data buffer 112B may be configured to store a number of the most recent measured values output by the set of sensing elements 112A. For example, the data buffer 112B may store the most recent 1, 2, 3, 4, 5, 6, 7, 8, 9, 10, 11, 12, 13, 14, 15, 16, 17, 18, 19, 20, 25, 30, 35, 40, 45, 50, or 100 measured values output by the set of sensing elements 112A. In some embodiments, the data buffer 112B may include a data structure storing the measured values output by the set of sensing elements 112A. For example, the data buffer 112B may include a matrix, in which each row or column of the matrix stores measured values output by a respective one of the set of sensing elements 112A. In another example, the data buffer 112B may include stacks, queues, trees, linked lists, any other suitable data structure for storing measured values output by the set of sensing elements 112A.

In some embodiments, the data buffer 112B may be configured to store measured values output by the set of sensing elements 112A as a function of time. The data buffer 112B may be configured to store a number of measured values output by each of the set of sensing elements 112A at points over a period of time. For example, the data buffer 112B may store values output by the set of sensing elements 112A at points in the last 5 seconds, 10 seconds, 30 seconds, 1 minute, 10 minutes, 1 hour, 12 hours, 24 hours, or other suitable period of time. In some embodiments, the period of time for which the data buffer 112B stores measured values output by the set of sensing elements 112A may be configurable. For example, a user may adjust the period of item. In another example, the period of time may be programmatically adjustable (e.g., according to the environment 100, time of day, and/or other function). In some embodiments, data buffer 112B may be configured to store raw data output from one or more of the sensing elements 112A. In other embodiments, data buffer 112B may be configured to store data output from one or more of the sensing units 112A that has been processed (e.g., filtered, averaged, scaled, etc.) prior to storage.

Although in the example embodiment of FIG. 1, the data buffer 112B is shown as being within the chemical sensing unit 112, in some embodiments, the data buffer 112B may be separate from the chemical sensing unit 112. For example, the data buffer 112B may be located on a remote data store (e.g., a cloud based database). In another example, the data buffer 112B may be located in storage of a separate device. For example, the data buffer 112B may be in memory of a computing device (e.g., a smartphone, computer, or other device) in communication with the chemical sensing unit 112 (e.g., through a communication network).

As shown in FIG. 1, the event detection system 114 receives data from the chemical sensing unit 112. In some embodiments, the event detection system 114 may be configured to receive measured values output by the set of sensing elements 112A. In some embodiments, the event detection system 114 may be configured to receive the measured values by retrieving the data from the data buffer 112B. For example, the event detection system 114 may retrieve measured voltage values output by the set of sensing elements 112A stored in the data buffer 112B.

In some embodiments, the event detection system 114 may be configured to identify, using data (e.g., measurements) received from the chemical sensing unit 112, occurrence of an event. The event detection system 114 may be configured to analyze measured values output by the sensing elements 112A to identify a pattern indicative of an occurrence of an event. In some embodiments, the event detection system 114 may be configured to identify a pattern indicative of the occurrence of the event by determining that the measured values meet a predetermined pattern indicative of the occurrence of the event. The event detection system 114 may be configured to process a set of measured values output by the set of sensing elements 112A to generate a set of information (also referred to herein as a "descriptor"). A descriptor may represent measurements at a timepoint that were output by the set of sensing elements 112A. As an illustrative example, for a set of m sensing elements, a set of measured values output by the sensing elements at a point in time may include m values (e.g., voltage signal values). The event detection system 114 may generate the descriptor using the set of m values. In some embodiments, the event detection system 114 may be configured to generate a descriptor by normalizing measured values output by the set of sensing elements 112A. A descriptor may store information that can be used to generate an inference about one or more chemical characteristics of the environment 100 (e.g., about a scent in the environment 100). Each element of a descriptor may be referred to as an "attribute". Example techniques for generating a descriptor are described herein with reference to FIG. 6.

In some embodiments, the event detection system 114 may be configured to analyze one or more descriptors to identify a pattern indicative of an occurrence of an event. For example, a descriptor may be an m-dimensional array storing a value corresponding to each of the set of sensing elements 112A. In this example, the event detection system 114 may determine if each of one or more values in the array is within a respective range to identify an occurrence of an event. In another example, the event detection system 114 may be configured to compare multiple descriptors over a period of time to identify a pattern indicative of the occurrence of an event. For example, the event detection system 114 may determine the occurrence of an event by: (1) determining a distance (e.g., a Euclidean distance) between a first descriptor corresponding to a first timepoint and a second descriptor corresponding to a second timepoint; and (2) identify the pattern indicative of the occurrence of the event when the distance is less than a threshold distance.

In some embodiments, the event detection system 114 may be configured to generate a set of features using measured values output by the set of sensing elements 112A over a period of time. For example, the event detection system 114 may generate the set of features using measured values output by the sensing elements 112A over a period of 30 seconds, 1 minute, 5 minutes, 30 minutes, 1 hour, 12 hours, 1 day, or other suitable period of time. In some embodiments, the event detection system 114 may be configured to use one or more descriptors to generate the set of features. The event detection system 114 may use the descriptor(s) to generate a chronological descriptor that represents a period (e.g., a window) of time. For example, the event detection system 114 may use descriptors generated from sets of measured values output by the sensing elements 112A over a period of 1 hour to generate a chronological descriptor for the hour. The event detection system 114 be configured to generate the set of features using the chronological descriptor. An example process for generating a set of features is described herein with reference to FIG. 6.

In some embodiments, the event detection system 114 may be configured to identify the pattern indicative of the occurrence of the event by: (1) generating a set of features using the measured values output by the set of sensing elements 112A; and (2) providing the set of features as input to a machine learning model (e.g., a neural network) to obtain output indicating whether a timepoint corresponds to an occurrence of an event. For example, the output of the machine learning model may be a classification indicating whether a timepoint corresponds to an occurrence of an event. The machine learning model may be trained to identify one or more patterns in the set of features indicative of the occurrence of an event.

In some embodiments, the event detection system 114 may be configured to use one or more machine learning models to detect respective event(s). Each of the machine learning model(s) may be trained to detect a respective event. For example, each of the machine learning model(s) may be trained to detect a respective event based on a set of features provided as input to the machine learning model(s). As an illustrative example, each of the machine learning model(s) may be trained to detect an occurrence of an event in which a respective scent is introduced into the environment 100 (e.g., due to chemical(s) being introduced into the environment 100).

In some embodiments, each of the machine learning model(s) may be a neural network. For example, each of the machine learning model(s) may be a convolutional neural network (CNN), a recurrent neural network (RNN), a long short-term memory (LSTM) neural network, an auto encoder (AE), or any other suitable type of neural network. In some embodiments, each of the machine learning model(s) may be a support vector machine (SVM), a logistic regression model, a decision tree model, a Gaussian process, or any other suitable machine learning model. In some embodiments, the event detection system 114 may use different types of machine learning models for detecting different events.

In some embodiments, the event detection system 114 may be configured to determine a reference state of the environment 100. The reference state may represent a state of the environment 100 at a time when an event has not occurred (e.g., as indicated by measured values output by the sensing elements 112A). For example, the reference state may represent the state of the elements 112A when the analytes 102 exposed to the set of sensing elements 112A do not trigger generation of an inference of the environment 100. As an illustrative example, the chemical sensing system 110 may be used to identify scents in a kitchen associated with stages in a sequence of cooking. In this example, a reference state of the environment 100 may be when the analytes 102 consist primarily of air without chemicals generated in a stage of the cooking.

In some embodiments, the event detection system 114 may be configured to generate an indication of a reference state of the environment 100 using a machine learning model. The event detection system 114 may be configured to: (1) generate a set of features using measured values output by the set of sensing elements 112A; and (2) provide the set of features as input to a trained machine learning model to obtain output. The output of the machine learning model may be the indication of the reference state. For example, the output may be a portion or all of a latent representation generated at a layer of a neural network that represents a reference state of the environment 100. As an illustrative example, the output may be a vector within the latent representation. In some embodiments, the event detection system 114 may be configured to generate the set of features by: (1) generating descriptors using measured values output by the set of sensing elements 112A; (2) generating one or more chronological descriptors using the descriptors (e.g., by grouping sets of descriptors to represent a period of time); and (3) generating the set of features using the chronological descriptor(s). In some embodiments, the machine learning model may be a neural network. For example, the neural network may be a convolutional neural network (CNN), a recurrent neural network (RNN), a long short-term memory (LSTM) neural network, an auto encoder (AE), or any other suitable type of neural network. In some embodiments, the machine learning model may be a support vector machine (SVM), a logistic regression model, a decision tree model, or any other suitable machine learning model.

In some embodiments, the event detection system 114 may be configured to identify a pattern indicative of an event by identifying a change from a reference state that indicates an occurrence of an event. The event detection system 114 may be configured to: (1) determine a current state of the environment 100 using measured values output by the set of sensing elements 112A; and (2) compare the current state of the environment 100 to the reference state. In some embodiments, the event detection system 114 may be configured to determine a current state by: (1) generating a set of features representing the current state; and (2) providing the set of features as input to a trained machine learning model to obtain output. The output may indicate whether there is a change from the reference state indicative of the occurrence of an event. In some embodiments, the machine learning model may receive as input: (1) an indication of the reference state (e.g., generated by another machine learning model); and (2) a set of features representing a current state. The machine learning model may be trained to determine whether a change from a reference state is indicative of the occurrence of an event. In some embodiments, the machine learning model may be a neural network. For example, the neural network may be a convolutional neural network (CNN), a recurrent neural network (RNN), a long short-term memory (LSTM) neural network, an auto encoder (AE), or any other suitable type of neural network. In some embodiments, the machine learning model may be a support vector machine (SVM), a logistic regression model, a decision tree model, or any other suitable machine learning model.

In some embodiments, the event detection system 114 may be configured to function as a switch that controls when information is sent to the inference system 116. In some embodiments, the information may include measured values output by the sensing elements 112A. The event detection system 114 may be configured to pass the measured output values to the inference system 116 when an event is detected. In some embodiments, the information may be descriptor(s) and/or chronological descriptor(s) generated by the event detection system 114 using measured values output by the set of sensing elements 112A. The event detection system 114 may be configured to pass the descriptor(s) and/or chronological descriptor(s) to the inference system 116 when an event is detected.

In some embodiments, the event detection system 114 may be configured to send reference state information to the inference system 116. The reference state information may be an indication of the reference state of the environment 100. The reference state information may be used in generating an inference about chemical characteristic(s) of the environment 100. In some embodiments, the indication of the reference state may be an output of a machine learning model. For example, the indication of the reference state may be a latent representation generated at a layer of a neural network that represents a reference state of the environment 100. In some embodiments, the event detection system 114 may be configured to periodically update the indication of the reference state and send the updated indication of the reference state to the inference system 116.

As indicated by the dotted arrow between the inference system 116 and the event detection system 114 shown in FIG. 1, in some embodiments, the event detection system 114 may receive information from the inference system 116. The event detection system 114 may be configured to use the information received from the inference system 116 to identify events. In some embodiments, the event detection system 114 may be configured to receive information about one or more inferences generated for one or more previously detected events. For example, the event detection system 114 may use the information about the inference(s) generated from the previously detected event(s) to update an indication of a reference state. In some embodiments, the information may include descriptors and/or chronological descriptors used to generate the inference(s). In some embodiments, the information may include information specifying that the descriptors, chronological descriptors, and/or set of features correspond to a state of the environment 100 when an event has not occurred. For example, the information may include information specifying that descriptors, chronological descriptors, and/or set of features correspond to analytes that do not correspond to an event.

In some embodiments, the inference system 116 may be configured to use information received from the event detection system 114 to generate an inference 118 about chemical characteristic(s) of the environment 100. For example, the inference system 116 may use measured values output by the sensing elements 112A to generate the inference 118 about chemical characteristic(s) of the environment. In another example, the inference system 116 may use descriptor(s) and/or chronological descriptor(s) generated by the event detection system 114 to generate the inference 118 about chemical characteristic(s) of the environment 100. In another example, the inference system 116 may use an indication of a reference state generated by the event detection system 114 to generate the inference 118 about chemical characteristic(s) of the environment 100. In another example, the inference system 116 may receive a signal (e.g., a Boolean value) that activates or deactivates generation of the inference 118.

As indicated by the dotted line from the chemical sensing unit 112 to the inference system 116 in FIG. 1, in some embodiments, the inference system 116 may receive measured values output by the set of sensing elements 112A. The inference system 116 may be configured to use the measured values with information received from the event detection system 114 to generate an inference 118. For example, the inference 118 may be a determined concentration of one or more chemicals in the environment 100 and/or an identification of a scent. In some embodiments, the inference system 116 may be configured to generate the inference 118 using: (1) an indication of a reference state of the environment 100 received from the event detection system 114; and (2) measured values output by the set of sensing elements 112A. For example, the inference system 116 may determine a current state of the environment 100 using the measured values output by the set of sensing elements and use the current state in conjunction with the indication of the reference state to generate the inference 118. In some embodiments, the inference system 116 may be configured to generate the inference 118 using the measured values output by the set of sensing elements 112A when the inference system 116 receives a command (e.g., a Boolean activation command) from the event detection system 114.

In some embodiments, the performance system 119 may be configured to use the inference output 118 generated by the inference system 116 may to trigger an action. In some embodiments, the performance system 119 may be configured to use the inference output 118 to generate a command (e.g., a software command) to perform an action. For example, the performance system 116 may generate, based on the inference output 118, a command to modify a temperature setting of a cooking range, release a substance (e.g., a deodorant) into the environment 100, activate an alarm, and/or instruct a user to perform an action. In another example, the performance system 119 may determine characteristic(s) of the state of the environment 100 based on the inference output 118. For example, the inference 118 may be used to indicate a scent that is present in the environment 100.

In some embodiments, the inference system 116 may be configured to generate an inference about stages of cooking a recipe (e.g., to perform functionality as a smart cooking assistant). For example, the inference system 116 may identify an odor based on sensed analytes 102, and determine the state of cooking the recipe based on the identified odor. The generated inference may be used to control one or more systems to automate cooking of the recipe. For example, based on a detected state of cooking the recipe, the cooking process may be adjusted (e.g., by modifying temperature of a stove). The event detection system 114 may be configured to identify a cooking stage by analyzing measured values output by the set of sensing elements 112A to identify a pattern indicative of the cooking stage. The event detection system 114 may be configured to periodically analyze the measured values to allow the performance system 119 to monitor the cooking process and/or trigger actions (e.g., to make programmatic adjustments to temperature).

In some embodiments, the inference system 116 may be configured to generate an inference about scents in the environment 100 for use in controlling a deodorant dispenser. The inference system 116 may be configured to generate an inference for use in determining whether deodorant should be released into the environment 100. For example, the inference system 116 may determine whether an odor in the environment 100 is sufficient to trigger release of a deodorant. The event detection system 114 may be configured to generate a reference state based on which the inference system 116 may generate an inference indicative of whether to release deodorant. The event detection system 114 may be configured to periodically analyze the measured values to allow the inference system 116 to have an updated reference state.

In some embodiments, the inference system 116 may be configured to generate an inference about spoilage of food (e.g., produce). For example, the inference system 116 may generate inference about whether the food is spoiled or not. The inference may be used by the performance system 119 to trigger a release of fungicides or to trigger an alarm that instructs a user to remove the spoiled food. The event detection system 114 may be configured to periodically analyze measured values output by the set of sensing elements 112A to allow the performance system 119 to automatically track fungal growth in the environment 100.

Although the example embodiment of FIG. 1 shows the event detection system 114, the inference system 116, and the performance system 119 as separate components of the chemical sensing system 110, in some embodiments, they may be modules of a single component of the chemical sensing system 110 (e.g., implemented by a single processor or collection of processors). In some embodiments, they may be separate systems. In some embodiments, the event detection system 114 and the inference system 116 may share one or more modules. In some embodiments, the event detection system 114 and the inference system 116 may be implemented as a single system. In some embodiments, the event detection system 114 and/or the inference system 116 may be separate from the chemical sensing unit 112. For example, the event detection system 114 and/or the inference system 116 may be computing devices remotely located relative to the chemical sensing unit 112. Data from the chemical sensing unit 112 may be sent to the event detection system 114 and/or the inference system 116 (e.g., through a communication network).

Figure 2A:
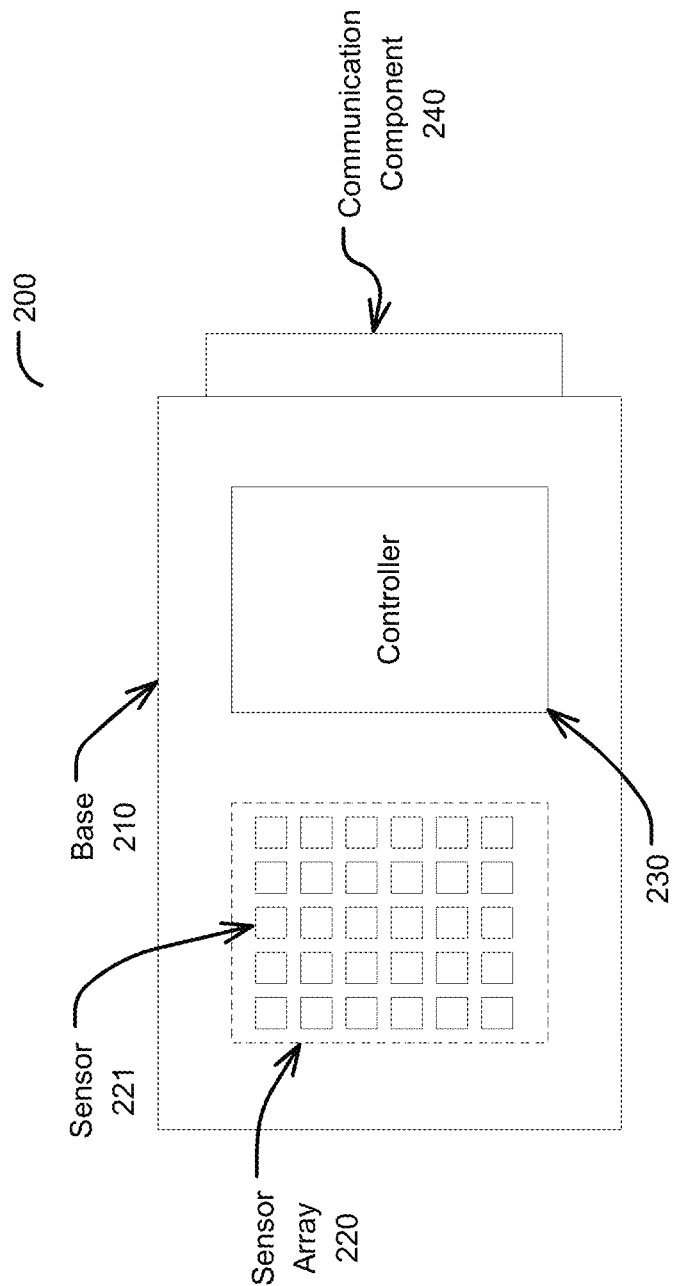
Figure 2B:
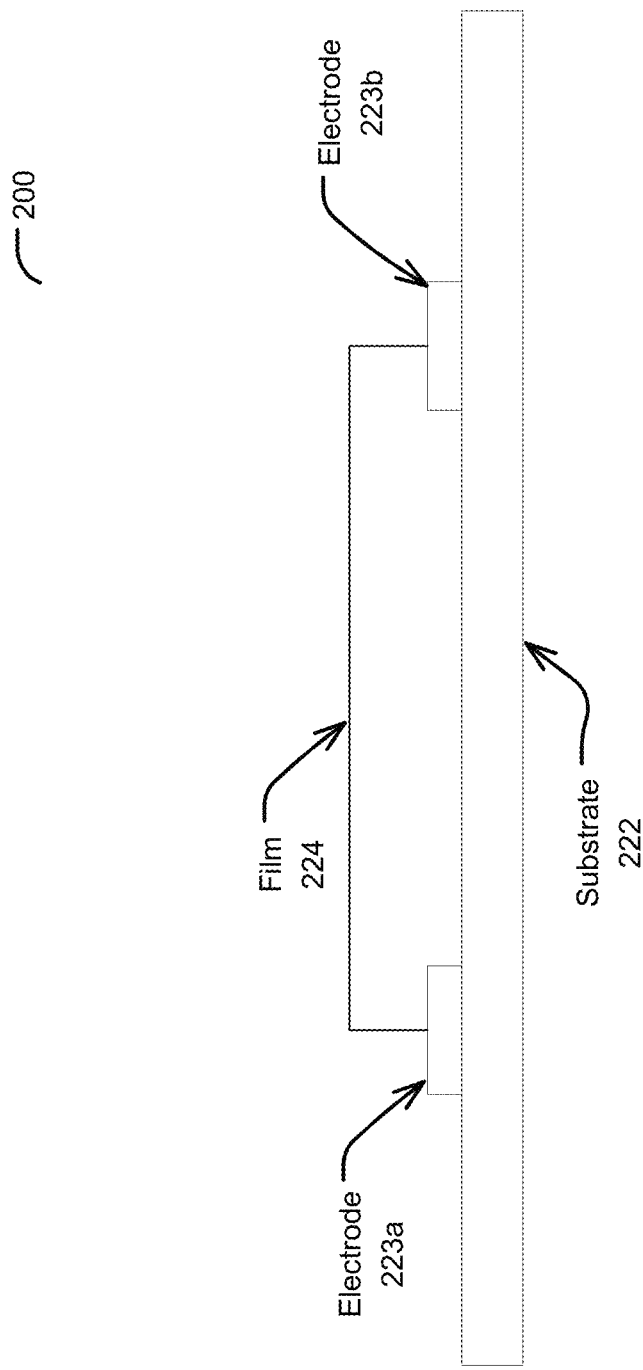

FIG. 2A and FIG. 2B depict views of an exemplary chemical sensing unit 200. Chemical sensing unit 200 includes an array of sensing elements 220. A sensing element may also be referred to as a "sensor", and the array of sensing elements 220 may also be referred to as a "sensor array". Individual outputs from a plurality of sensing elements in the array may exhibit incomplete information about the chemical species in the environment in which the chemical sensing unit is placed. For example, each output may exhibit a dependence on multiple, time varying extraneous variables (e.g., temperature, humidity, etc.) that are not well specified based on the output of that sensor alone. By including multiple sensing elements in an array, the chemical sensing system may be configured to estimate the chemical composition of an environment using multiple output signals generated by the multiple sensing elements in the array. For example, the chemical sensing system may process the output from multiple sensing elements in an array using an inferential model to generate an estimate of a concentration of one or more chemicals in the environment.

Chemical sensing unit 200 includes a base 210 configured to support a sensor array 220. Base 210 may be implemented using any suitable substrate including, but not limited to, a circuit board. The sensor array 220 includes a plurality of sensors (e.g., sensor 221). The sensors may be arranged in rows and columns, as shown, or the sensors may be arranged in another arrangement (e.g., concentric circles, staggered rows, etc.). The described location and orientation of the sensors on chemical sensing unit 200 are not intended to be limiting.

Chemical sensing unit 200 includes a controller 230. In some embodiments, controller 230 is configured to provide power to the plurality of sensors. In some embodiments, controller 230 is configured to acquire signals from the plurality of sensors. For example, each of the sensors may include, or be a part of, a Wheatstone bridge or another circuit configured to measure changes in resistance. Controller 230 may be configured to provide power for the sensors and/or acquire signals from the sensors corresponding to changes in resistance measured by the sensors. In some embodiments, controller 230 is further configured to provide one or more of signal conditioning, signal processing, and signal communication. For example, controller 230 may be configured to filter and amplify signals received from the sensors. In some embodiments, controller 230 is further configured to perform at least some of the mapping operations described in more detail below. For example, controller 230 may be configured to implement one or more models relating the signals output by the sensors to a latent representation, or to an output representation having one or more axes corresponding to relevant analytes. In some embodiments, controller 230 includes at least one storage device (e.g., a memory) configured to store parameters that define one or more of the mapping operations, described in more detail below.

Chemical sensing unit 200 includes a communications component 240, which can include hardware and/or software configured to enable chemical sensing unit 200 to communicate with other elements of the chemical sensing unit (or other devices) (e.g., an event detection system and/or an inference system). For example, communications component 240 may include a network controller configured to provide local area network connectivity, a port controller configured to provide parallel port and/or serial port connectivity, and/or a wireless controller configured to provide WIFI, BLUETOOTH, ZIGBEE or similar connectivity.

As shown in FIG. 2B, in some embodiments, a sensor (e.g., sensor 221) includes a substrate 222 and one or more electrodes (e.g., electrodes 223a and 223b) disposed on substrate 222. In one implementation of sensor 221, a conductive film 224 is disposed on and between electrodes 223a and electrodes 223b as shown. For example, film 224 can include conductive nanoparticles. In some embodiments, film 224 is chemically sensitive. For example, film 224 may undergo a physical change (e.g., swelling, contracting, and/or a change in composition or state) upon exposure to an analyte. The physical change in the film 224 may result in a change in resistance between electrode 223a and electrode 223b. Controller 230 may be configured to monitor the resistance between electrode 223a and electrode 223b, resulting in an output signal from the sensor that is detectable by controller 230. The output signal may include semantic information concerning one or more analytes introduced to the sensor.

In some embodiments, one or more of the sensors in sensor array 220 are configured with differing sensitivities to different analytes or classes of analytes. For example, films for different sensors in the array may be configured to provide different degrees of physical change in response to exposure to the same analyte. As an additional example, a film for a sensor can be configured to provide different degrees of physical change in response to exposure to different analytes. Accordingly, in some embodiments, the output signals from different sensors in the array may differ in the presence of the same analyte and/or the output signal from the same sensor may differ in the presence of different analytes in the environment. These differences may include, but are not limited to, differences in amplitude and/or temporal characteristics of the output signal.

FIG. 2C shows an exemplary chemical sensing system 250, which may include chemical sensing units 200 and, optionally, an external storage medium 290. For example, the chemical sensing system 250 may be chemical sensing system 110 described herein with reference to FIG. 1. Each of the chemical sensing units 200 may be designed in the manner described herein at least with respect to FIGS. 2A-B. As depicted in FIG. 2C, the chemical sensing units 200 of chemical sensing system 250 may be capable of communicating with one another, such as by using the communications component 240 included in each chemical sensing unit, or any other suitable channel of communication. This communication channel may be utilized to share information such as training data, model information, or output signals between the chemical sensing units 200. For a given chemical sensing unit 200, the shared information may be stored, for example, on a storage device associated with the controller 230 of the chemical sensing unit or on external storage medium 290.

As shown in FIG. 2C, external storage medium 290 may be accessible by the chemical sensing units 200 via their communications components 240. The external storage medium 290 need not be a single storage device, but may be distributed over a number of devices, such as in a cloud storage configuration. In some cases, one or more of the chemical sensing units 200 may store information such as training data, model information, or output signals on the external storage medium 290. One or more of the chemical sensing units 200 may also access information from the external storage medium 290, not limited to information stored by the chemical sensing units on the external storage medium, including training data, model information, output signals, or other information.

Figure 3:
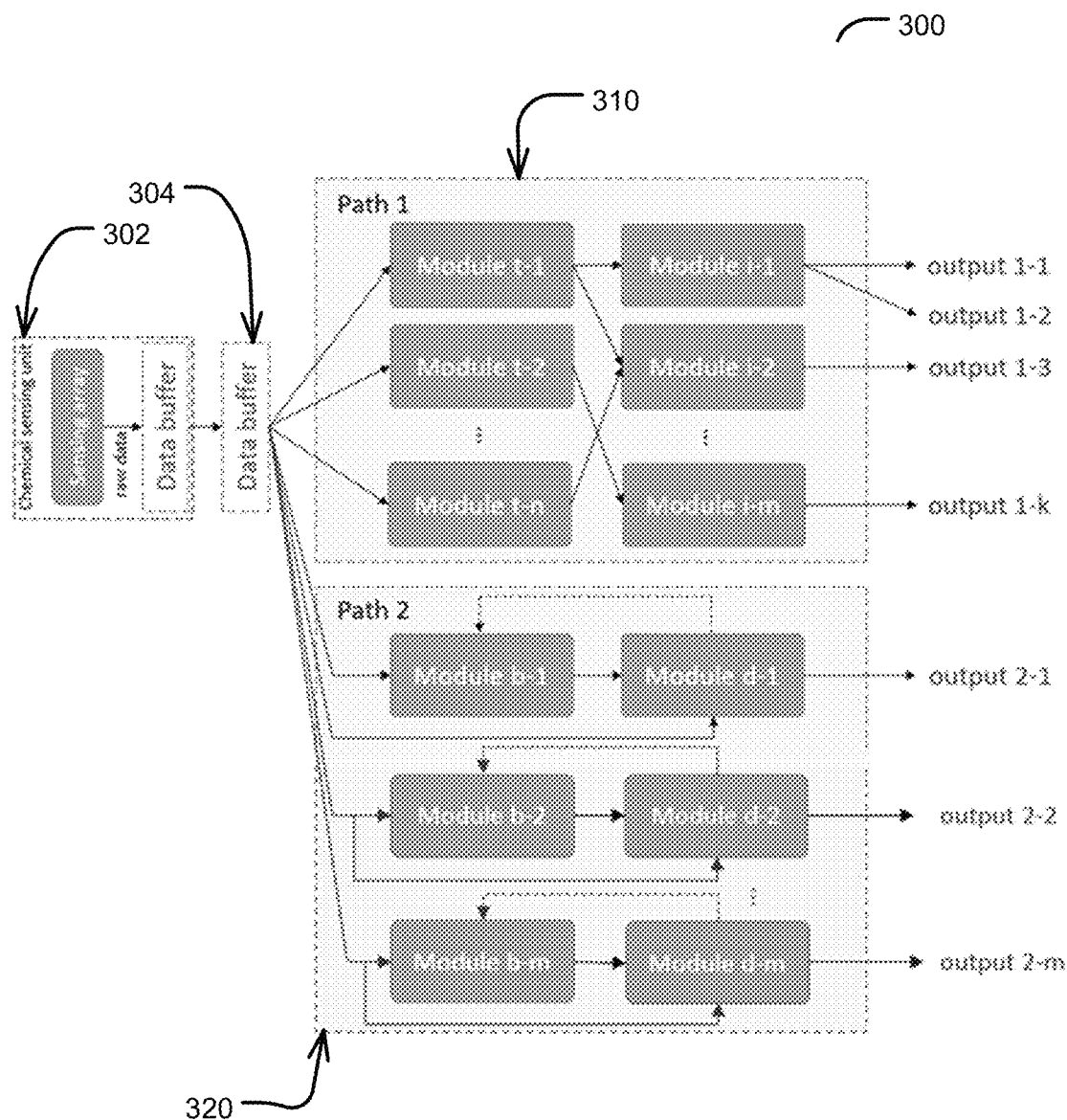
FIG. 3 illustrates a data flow diagram for generating an inference based on detection of an event, according to some embodiments of the technology described herein.

FIG. 3 illustrates a data flow diagram 300 for generating an inference based on detection of an event, according to some embodiments of the technology described herein. As shown in FIG. 3, the chemical sensing unit 302 sends measurement data (e.g., measured values output by a set of sensing elements) to a data buffer 304. In some embodiments, the chemical sensing unit 302 may be chemical sensing unit 112 described herein with reference to FIG. 1. Each of the components 310, 320 may comprise the event detection system 114 and the inference system 116.

As shown in FIG. 3, the component 310 includes event detection modules $t_1$-$t_n$. Each of the event detection modules may be a module of the event detection system 114 described herein with reference to FIG. 1. In some embodiments, each of the modules $t_1$-$t_n$ may be configured to identify a start of a respective event. The module $t_1$ may be configured to identify, using the measurements, a start of a first event, and the module $t_2$ may be configured to identify, using the measurements, a start of a second event different from the first event. As an illustrative example, the module $t_1$ may be configured to detect the start of a first stage of cooking a recipe while the module $t_2$ may be configured to detect a start of a second stage of cooking a recipe.

In some embodiments, each of the modules "t-1" to "t-n" may be configured to detect a respective event by identifying, using the measurement data, a timepoint corresponding to a start of the event. The module may be configured to analyze measured values output by the chemical sensing unit 302 (e.g., by sensing elements of the chemical sensing unit 302). The module may be configured to identify a pattern indicative of the occurrence of the event. In some embodiments, the module may include a machine learning model trained to generate an output for a set of features input to the machine learning model. The output may indicate whether an occurrence of an event is detected. For example, the module "t-1" may be trained to generate an output indicating whether a particular stage of cooking a recipe (e.g., cooking meat) is starting. Example processes by which the module may identify a timepoint corresponding to an occurrence of an event are described herein with reference to FIGS. 4-7.

As shown in FIG. 3, each of the modules "t-1" to "t-n" may be coupled to a respective one or more of the inference modules "i-1" to "i-m". Each of the inference modules "i-1" to "i-m" may be configured to generate an inference using measurements from the chemical sensing unit 302. In some embodiments, the inference module may be configured to receive information from a respective event detection module. For example, the inference module may receive measurements from the event detection module and/or information generated using the measurement data (e.g., descriptor(s), chronological descriptor(s), and/or set of features). The inference module may use the information received to generate an inference. Accordingly, in some embodiments, an event detection module may function as a switch that allows or prevents information from reaching respective inference module(s). In some embodiments, the inference module may be configured to receive an activation signal from respective event detection module(s) that triggers generation of an inference by the inference module using the measurement data.

As shown in FIG. 3, each of the inference module "i-1" to "i-m" may be configured to generate one or more inference outputs. Module $i_1$ generates inference outputs "1-1", "1-2", module "i-2" generates inference output "1-3", and module "i-m" generates inference output "1-$k$". In some embodiments, the output may indicate information about an environment. For example, the output may indicate a concentration of one or more chemicals in the environment and/or identify a scent present in the environment. In some embodiments, the output may indicate a command for an action. For example, the output may trigger a programmatic action by another system (e.g., automatically adjusting a temperature setting of a stove).

As shown in FIG. 3, the component 320 includes event detection modules "b-1" to "b-n". Each of the event detection modules may be a module of the event detection system 114 described herein with reference to FIG. 1. In some embodiments, each of the modules "b-1" to "b-m" may be configured to generate an indication of a reference state of the environment for a respective event. A sufficient change from the reference state may result in identification of an occurrence of an event. The module "b-1" may be configured to generate, using the measurements, a first reference state, and the module "b-2" may be configured to generate, using the measurement data, a second reference state different from the first reference state. As an illustrative example, the module "b-1" may be configured to generate a first reference state with respect to cooking a first stage of a recipe (e.g., cooking meat), and the module "b-2" may be configured to generate a second reference state with respect to cooking a second stage of the recipe (e.g., cooking rice).

In some embodiments, each of the modules "b-1" to "b-n" may be configured to generate a respective indication of a reference state using measurements. The module may be configured to analyze measured values output by the chemical sensing unit 302 (e.g., by sensing elements of the chemical sensing unit 302). In some embodiments, the module may include a machine learning model trained to generate an output for a set of features input to the machine learning model that indicates a reference state. For example, the module bi may be trained to generate a reference state for a first stage of cooking a recipe (e.g., cooking meat). An example process by which the module may generate a reference state is described herein with reference to FIG. 9.

As shown in FIG. 3, each of the event detection modules "b-1" to "b-m" may be coupled to a respective one or more of the inference modules "d-1" to "d-m". Each of the inference modules "d-1" to "d-m" may be configured to generate an inference using measurement data output from the chemical sensing unit 302. In some embodiments, the inference module may be configured to receive an indication of a reference state from a respective event detection module. For example, the inference module may receive a set of values representing a reference state from the event detection module. The inference module may use the information received to generate an inference. In some embodiments, the inference module may be configured to use the information received to generate a portion of a set of features to provide as input to a machine learning model. As indicated by the arrows from the data buffer 304 to the inference modules "d-1" to "d-m", each of the inference modules "d-1" to "d-m" may be configured to receive measurements (e.g., measured values output by sensing elements) output by the chemical sensing unit 302. The inference module may be configured to use the measurements to generate a portion of the set of features. The inference module may be configured to provide the set of features as input to the machine learning model to obtain an inference output. The machine learning model may be trained to generate an inference based on the set of features. For example, the machine learning model may generate an inference for an event based on an identified change from a reference state received from a respective one of the event detection modules "b-1" to "b-m".

As indicated by the dotted line from each of the inference modules "d-1" to "d-m" to a respective one of the event detection modules "b-1" to "b-m", in some embodiments, an event detection module may be configured to use information from a respective inference module to generate an indication of a reference state. The event detection module may be configured to update the indication of the reference state based on information received from the inference module. For example, the indication of the reference state may be updated after an event (e.g., as the reference state of the environment 100 is different after the event). In another example, the indication of the reference state may be updated due to changes in ambient conditions (e.g., temperature and/or humidity) in an environment of a chemical sensing system.

As shown in FIG. 3, each of the inference modules "d-1" to "d-m" may be configured to generate one or more inference outputs. Module "d-1" generates inference output "2-1", module "d-2" generates inference output "2-2", and module "d-m" generates inference output "2-$m$". In some embodiments, the output may indicate information about an environment. For example, the output may indicate a concentration of one or more chemicals in the environment and/or identify a scent present in the environment. In some embodiments, the output may indicate a command for an action. For example, the output may trigger a programmatic action by another system (e.g., automatically adjusting a temperature setting of a stove).

It should be appreciated that in component 310, an inference module may be configured to generate an inference when triggered by a respective event detection module (e.g., when the event detection module identifies an occurrence of an event). In contrast, in the component 320, an inference module may be configured to generate an inference using an indication of a reference state provided by a respective event detection module without being triggered by the event detection module. For example, the inference module may periodically generate an inference output using an indication of the reference state provided by a respective event detection module. In some embodiments, a chemical sensing system may include both components 310 and 320. In some embodiments, a chemical sensing system may include component 310 but not component 320. In some embodiments, a chemical sensing system may include component 320 but not component 310.

Figure 4:
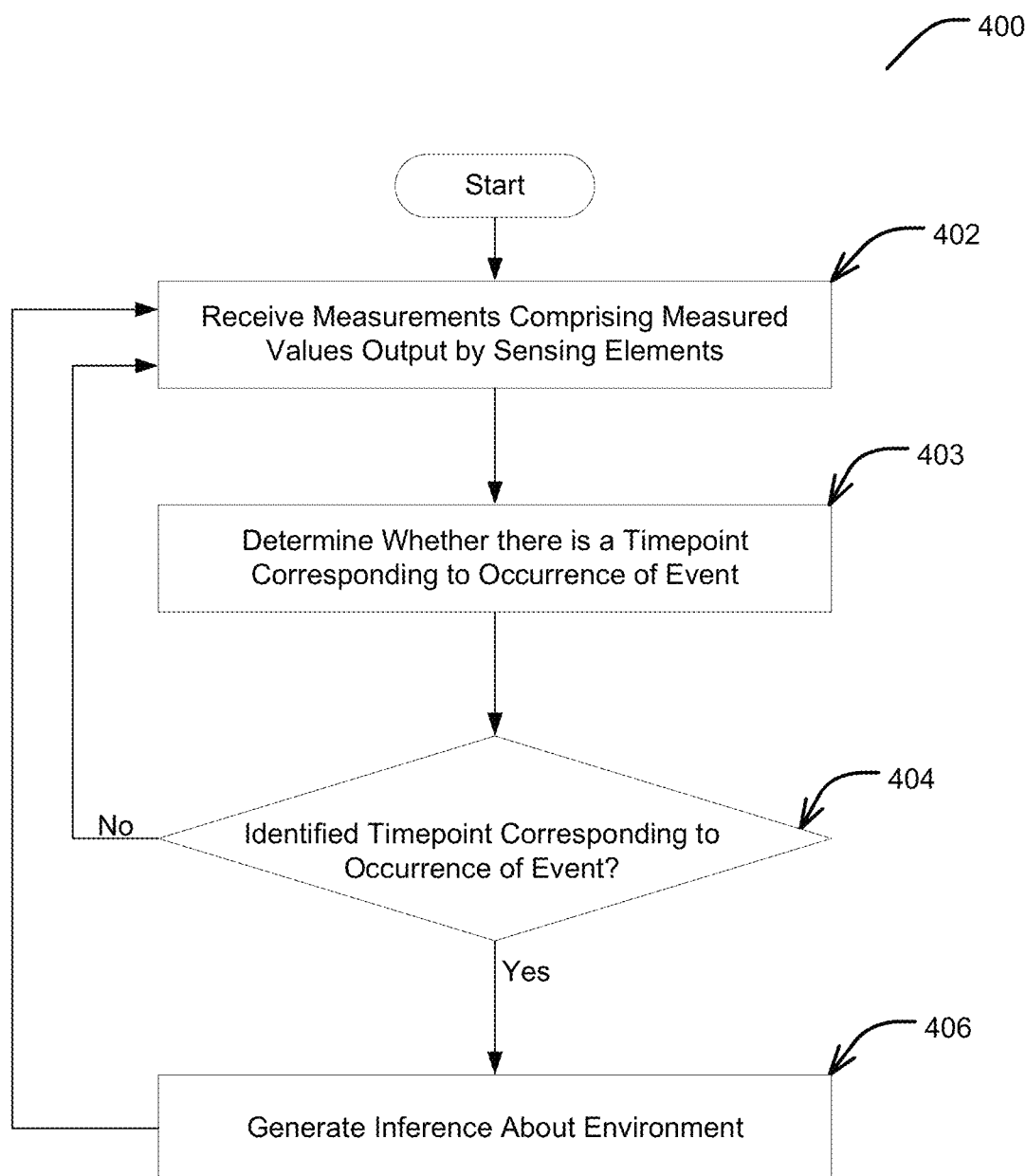
FIG. 4 illustrates a flowchart of an example process of generating an inference about one or more chemical characteristics of an environment, according to some embodiments of the technology described herein.

FIG. 4 illustrates a flowchart of an example process 400 of generating an inference about one or more chemical characteristics of an environment, according to some embodiments of the technology described herein. In some embodiments, process 400 may be performed by chemical sensing system 110 described herein with reference to FIG. 1. In some embodiments, process 400 may be performed by component 310 and/or component 320 described herein with reference to FIG. 3.

In some embodiments, process 400 may be performed to allow the chemical sensing system to generate inference(s) without input from a user indicating the start of an inference event. The process 400 may allow the chemical sensing system to be deployed in an environment and automatically generate inferences about chemical characteristic(s) of the environment. For example, the process 400 may be performed by a chemical sensing system deployed in an environment to detect mold growth. In another example, the process 400 may be performed by a chemical sensing system deployed in a kitchen to generate inferences about cooking in the kitchen (e.g., for use in programmatically guiding one or more appliances). In another example, the process 400 may be performed by a chemical sensing system deployed in a restroom facility to generate inferences about odors in the restroom facility (e.g., for use in controlling release of a deodorant).

Process 400 begins at block 402, where the system receives measurements comprising measured values output by sensing elements (e.g., sensing elements 112A of chemical sensing unit 112). In some embodiments, the system may be configured to receive the measurements by obtaining them from memory (e.g., buffer 112B) storing measured values output by the sensing elements. For example, the system may read the measured values stored in the memory. In some embodiments, the system may be configured to receive measured values output by the sensing elements at points in a period of time. For example, the sensing elements may output measured values periodically (e.g., every 1 minute, 10 minutes, 1 hour, 2 hours, 12 hours, etc.) for storage in memory. The system may be configured to read the measured values from memory.

Next, process 400 proceeds to block 403, where the system determines whether there is a timepoint corresponding to an occurrence of an event. The system may be configured to determine whether there is a timepoint corresponding to the occurrence of an event by analyzing the measured values to identify a pattern indicative of an occurrence of an event. In some embodiments, the system may be configured to analyze the measured values to identify the pattern by using the measured values to generate a set of features. The system may be configured to use the set of features to determine whether the measured values output by the sensing elements meet a pattern indicative of the occurrence of the event. An example process for generating a set of features is described herein with reference to FIG. 6.

In some embodiments, the system may be configured to generate a set of features that represent measurements output from a timepoint. For example, the system may generate the set of features using measured values output by sensing elements at the timepoint. In some embodiments, the system may be configured to generate the set of features using measured values output by sensing elements in a time window including timepoints before and/or after the timepoint. For example, the system may generate the set of features using measured values output by sensing elements in a time window centered at the timepoint. The time window may be 5 seconds, 30 seconds, 1 minute, 10 minutes, 1 hour, 2 hours, 12 hours, 24 hours, or other length of time. In some embodiments, the system may be configured to provide the set of features as input to a machine learning model to obtain output indicating whether a timepoint corresponds to an occurrence of an event. The machine learning model may be trained to identify a pattern indicative of the occurrence of the event. An example process for using a set of features to identify a timepoint corresponding to an occurrence of an event is described herein with reference to FIG. 5.

In some embodiments, the system may be configured to determine an indication of a reference state of the environment. The reference state may be a state of the environment (e.g., as indicated by measured values output by sensing elements) at a time when an event has not occurred. The system may be configured to use the indication of the reference state to identify a timepoint corresponding to the occurrence of an event. In some embodiments, the system may be configured to generate a set of features using measured values output by the sensing elements and the indication of the reference state to identify the timepoint corresponding to the occurrence of the event. The system may be configured to use the set of features to identify a change from the reference state indicative of the occurrence of the event. In some embodiments, the system may be configured to provide the set of features as input to a machine learning model trained to generate an output indicating whether there is a change from the reference state indicative of the occurrence of an event. An example process of generating an inference based on identification of a change from a reference state is described herein with reference to FIG. 7.

Next, process 400 proceeds to block 404, where the system determines whether a timepoint corresponding to an occurrence of an event has been identified. If the system does not identify a timepoint corresponding to the occurrence of an event at block 404, then process 400 proceeds to block 402 where the system receives measurements (e.g., from a chemical sensing unit). In some embodiments, the system may be configured to receive a new set of measurements. For example, the system may receive measurements output by sensing elements over a period of time subsequent to a period of time in which the previous measurements were output.

If the system identifies a timepoint corresponding to the occurrence of an event at block 404, then process 400 proceeds to block 406, where the system generates an inference about chemical characteristic(s) of the environment. The system may be configured to generate an inference about the chemical characteristic(s) of the environment using measurements obtained before and/or after the first time point. The measurements may include measured values output by the sensing elements after the identified timepoint. The measurements may provide information about one or more chemicals in the environment after a detected start of an event. The system may be configured to use the information to generate an inference about chemical characteristic(s) of the environment. For example, the system may use the measurements to generate an inference of a concentration of one or more chemicals in the environment. In another example, the system may use the measurements to generate an inference identifying a scent present in the environment. In another example, the system may use the measurements to generate an inference identifying a stage of cooking.

In some embodiments, the system may be configured to use the measurements obtained before and/or after the first timepoint to generate a set of features representing the event. An example process for generating a set of features is described herein with reference to FIG. 6. The system may be configured to provide the generated set of features as input to a machine learning model to obtain an output. In some embodiments, the machine learning model may be a neural network. For example, the neural network may be a CNN, RNN, LSTM, or other suitable type of neural network. In some embodiments, the machine learning model may be a different type of machine learning model described herein.

In some embodiments, a machine learning model used to generate the inference at block 406 may be different than a machine learning model used to identify the timepoint corresponding to the occurrence of an event. For example, the system may use a first machine learning model (e.g., a first neural network) to identify the timepoint corresponding to the occurrence of the event, and a second machine learning model (e.g., a second neural network) to generate the inference. In some embodiments, a machine learning model used to identify the timepoint corresponding to the occurrence of the event may also be used to generate the inference about chemical characteristic(s) of the environment at block 406. For example, the system may use the measurements and an indication of a reference state to generate input to the machine learning model. The machine learning model may generate an output indicating an occurrence of an event and an inference about chemical characteristic(s) of the environment.

After generating the inference about chemical characteristic(s) of the environment at block 406, process 400 returns to block 402, where the system receives new measurements (e.g., from sensing elements of a chemical sensing unit). The system may use the new measurements to identify a timepoint corresponding to an occurrence of an event as described at block 404 and/or generate an inference about chemical characteristic(s) of the environment as described at block 406. Accordingly, the system may be configured to continuously monitor the environment to identify events and generate inferences about chemical characteristic(s) of the environment. For example, the system may be deployed in the environment and perform process 400 without requiring input from a user.

In some embodiments, the system may be configured to identify an end of an event. The system may be configured to identify a timepoint corresponding to the end of the event. The system may be configured to identify a timepoint corresponding to the end of an event by analyzing the measured values to identify a pattern indicative of an end of an event. In some embodiments, the system may be configured to analyze the measured values to identify the pattern by using the measured values to generate a set of features. The system may be configured to use the set of features to determine whether the measured values output by the sensing elements meet a pattern indicative of the end of the event. An example process for generating a set of features is described herein with reference to FIG. 6. In some embodiments, the system may be configured to provide the set of features as input to a machine learning model to obtain output indicating whether a timepoint corresponds to an end of an event. The machine learning model may be trained to identify a pattern indicative of the end of the event. The set of features may be used to identify the end of the event using process 500 described herein with reference to FIG. 5, but for identification of the end of the event instead of the start.

In some embodiments, the system may be configured to use an indication of the reference state to identify a timepoint corresponding to the end of an event. In some embodiments, the system may be configured to generate a set of features using measured values output by the sensing elements and the indication of the reference state to identify the timepoint corresponding to the end of the event. The system may be configured to use the set of features to identify a change to return to the reference state indicative of the end of the event. In some embodiments, the system may be configured to provide the set of features as input to a machine learning model trained to generate an output indicating whether there is a change from the reference state indicative of the end of an event.

In some embodiments, the system may be configured to use the identified end of the event to generate an inference about the environment at block 406. For example, the system may identify measurements output between the timepoint corresponding to the occurrence of the event and the timepoint corresponding to the end of the event to generate a set of features that are used to generate the inference about the environment.

Figure 5:
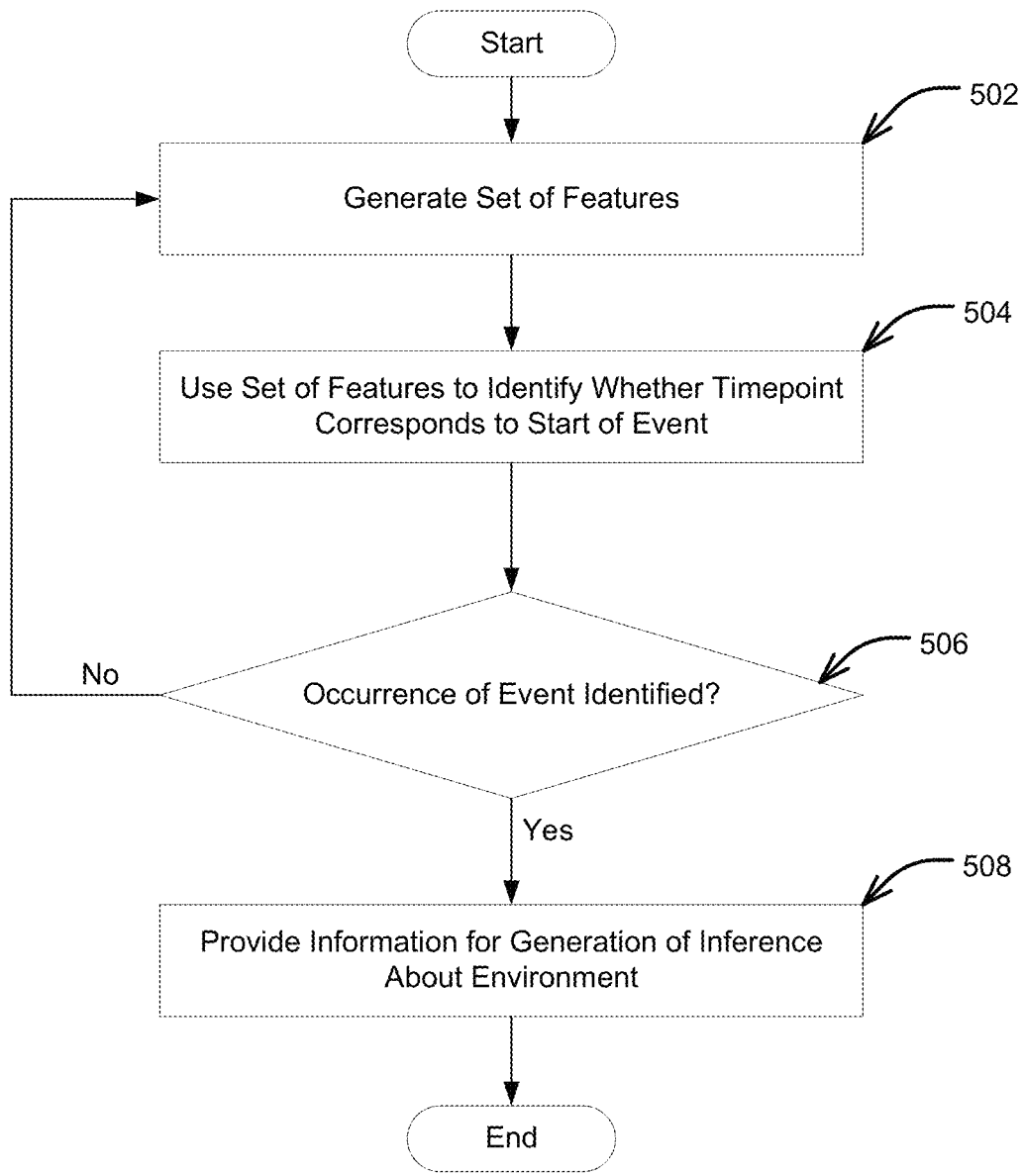
FIG. 5 illustrates a flowchart of an example process of generating an inference about chemical characteristic(s) of an environment based on detection of an event, according to some embodiments of the technology described herein.

FIG. 5 illustrates a flowchart of an example process 500 of generating an inference about chemical characteristic(s) of an environment based on detection of an event, according to some embodiments of the technology described herein. Process 500 may be performed by chemical sensing system 110 described herein with reference to FIG. 1. For example, process 500 may be performed by event detection system 114 of the chemical sensing system 110. In some embodiments, process 500 may be performed by an event detection module of component 310 described herein with reference to FIG. 3.

Process 500 begins at block 502, where the system performing process 500 generates a first set of features. In some embodiments, the system may be configured to generate the first set of features using a first set of measurements comprising measured values output by sensing elements (e.g., of chemical sensing unit 112). The system may be configured to generate the set of features as described herein with reference to FIG. 6. The first set of features may represent a state of the environment based at least on measurements sensed at a timepoint.

Next, process 500 proceeds to block 504, where the system uses the first set of features to determine whether the timepoint corresponds to an occurrence of an event. In some embodiments, the system may be configured to use the first set of features to determine whether the timepoint corresponds to the occurrence of an event by providing the set of features as input to a machine learning model to obtain output indicating whether a timepoint corresponds to an occurrence of an event. The machine learning model may be trained to identify one or more patterns representing an occurrence of an event (e.g., as described herein with reference to FIG. 8). The machine learning model may output, for example, a classification indicating whether the timepoint corresponds to an occurrence of an event (e.g., a scent detection event, a cooking state, or other type of event). For example, the machine learning model may be a neural network (e.g., a CNN, RNN, LSTM, or other type of neural network) that outputs a classification indicating whether the timepoint corresponds to an occurrence of an event. In this example, the system may provide the set of features as input values to an input layer of the neural network. Other examples of machine learning models that may be used are described herein.

In some embodiments, the system may be configured to determine if the set of features meets a predetermined pattern representing an occurrence of an event without using a machine learning model. For example, the system may determine a measure of distance (e.g., Euclidean distance) between the set of features and a set of features representative of an occurrence of an event to determine if the set of features are indicative of an event. In some embodiments, the system may be configured to analyze a relationship between respective values in the set of features to determine if the set of features matches a predetermined pattern representing an occurrence of an event. For example, the system may: (1) determine a measure of distance between a first subset of the set of features and a second subset of the set of features; and (2) determine if the set of features meets the predetermined pattern representing the occurrence of the event when the measure of distance is greater than a threshold distance.

Next, process 500 proceeds to block 506, where the system determines whether an occurrence of an event is identified. The system may be configured to use a result of processes performed at block 504 to determine whether an occurrence of an event has been identified. In some embodiments, the system may be configured to use an output of a machine learning model (e.g., a neural network) to determine whether an event has been identified. For example, the system may determine that an occurrence of an event has been identified when a classification output (e.g., a binary classification) of the machine learning model indicates that the timepoint corresponds to the occurrence of an event. In another example, the system may determine that the occurrence of an event has been identified when the first set of features are determined to have a pattern matching a predetermined pattern indicative of an occurrence of an event.

Figure 9:
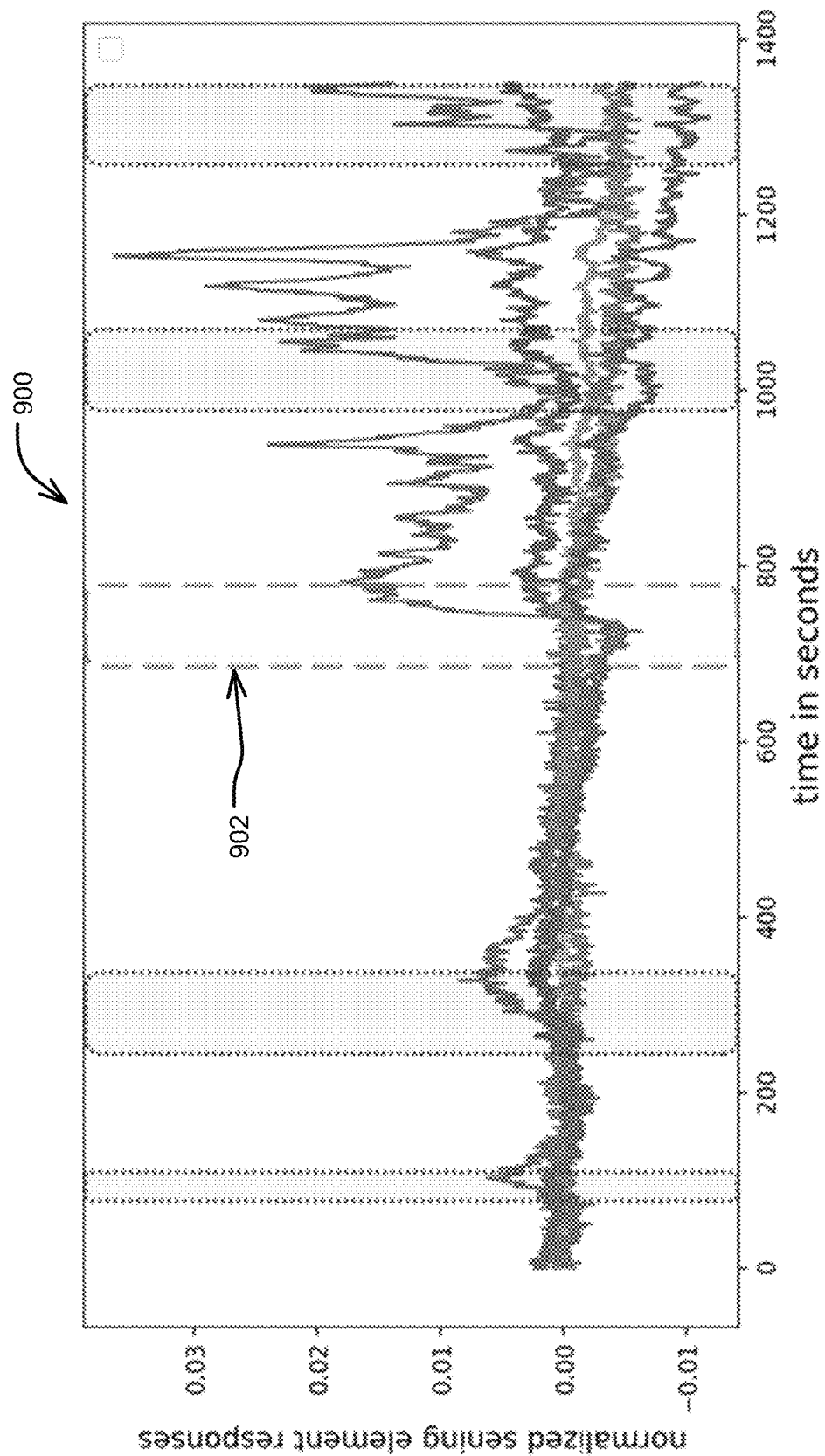
FIG. 9 illustrates a graph depicting identification of a pattern indicative of the occurrence of an event, according to some embodiments of the technology described herein.

FIG. 9 illustrates a graph 900 depicting identification of a pattern indicative of the occurrence of an event, according to some embodiments of the technology described herein. The graph 900 shows normalized measured values output by multiple sensing elements with respect to time. The time window 902 of the graph 900 depicts a window of time in which an occurrence of an event has been detected. As can be seen in FIG. 9, an output signal of one of the sensing elements shows an increase from a value of less than 0.00 to a value above 0.01 during the time window 902. The system performing process 500 may identify a timepoint in the time window 902 at which the output signal of the sensing element increases as corresponding to an occurrence of an event (e.g., using an output of a machine learning model). Although the example of FIG. 9 depicts a visually perceptible change in an output signal indicative of the occurrence of an event, in some cases the change in the output signal may not be as distinct relative to output signals of other sensing elements. Accordingly, a machine learning model may use output signals of multiple sensing elements to identify a pattern among the output signals indicative of an occurrence of an event.

If the system determines that the occurrence of an event has not been identified at block 506, then process 500 proceeds to block 502, where the system generates a new set of features. The system may be configured to generate a new set of features representing a state of the environment at a subsequent timepoint. If the system determines that the occurrence of the event has been identified at block 506, then process 500 proceeds to block 508, where the system provides information for generation of inference about chemical characteristic(s) of an environment (e.g., to inference system 116). In some embodiments, the system may be configured to provide information including measurements based on the identified timepoint. The measurements may include measurements obtained before and/or after the timepoint identified as corresponding to an occurrence of an event. Thus, the measurements may be used to generate an inference about chemical characteristic(s) (e.g., concentration of chemical(s), identification of a scent, or other characteristic) of the environment (e.g., environment 100). The information provided at block 508 may be used to generate an inference about chemical characteristic(s) of the environment. For example, the information provided at block 508 may be used to generate a second set of features to provide as input to a machine learning model to generate the inference.

In some embodiments, the system may be configured to generate a second set of features. The system may be configured to generate the second set of features using measurements output by the sensing elements before and/or after the timepoint identified as corresponding to an occurrence of an event. In some embodiments, the system may be configured to generate the second set of features using only measurements output after the timepoint. In some embodiments, the system may be configured to generate the second set of features using measurements output after the timepoint and measurements output prior to the timepoint. The system may be configured to provide the second set of features for generation of the inference (e.g., for input to a machine learning model).

Figure 6:
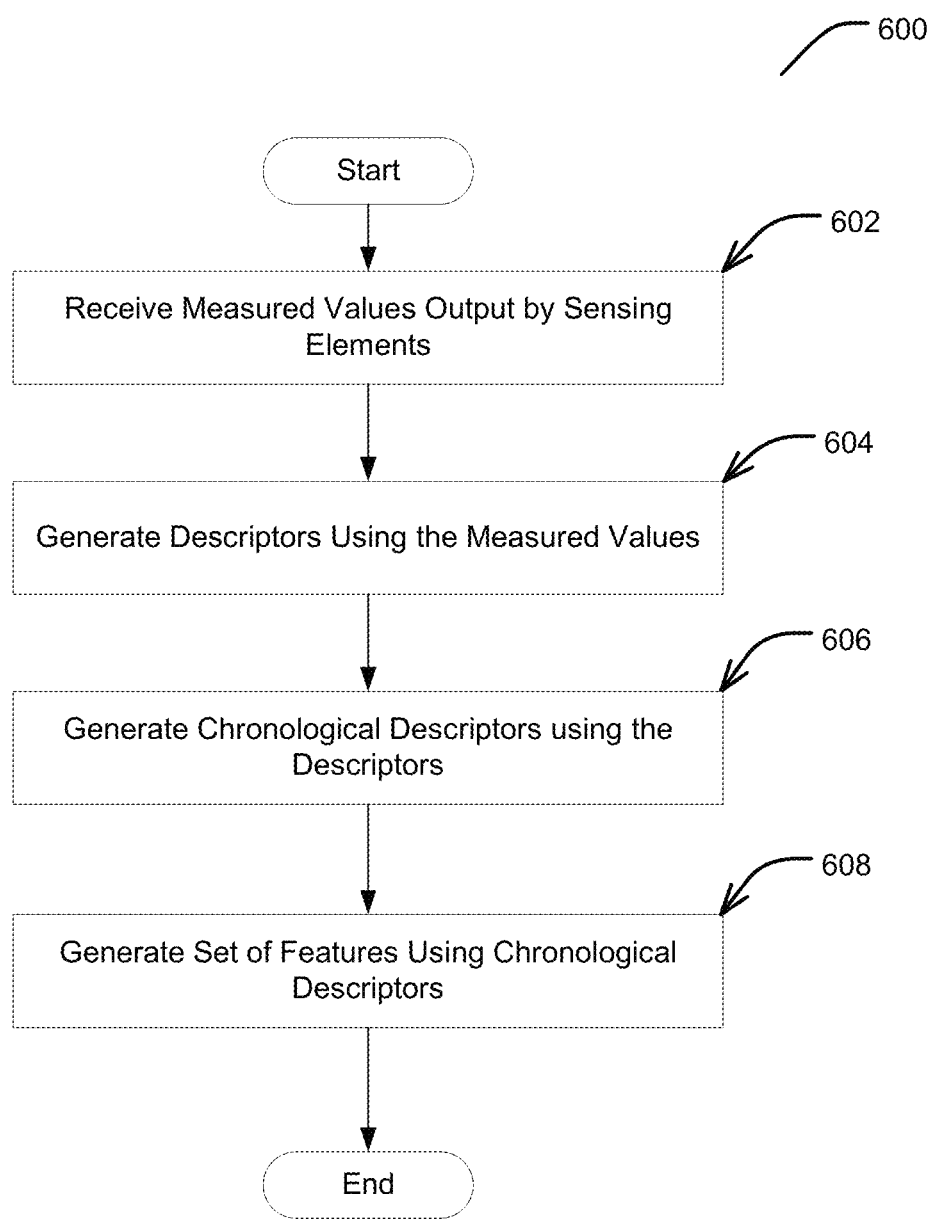
FIG. 6 illustrates a flowchart of an example process of generating a set of features using measured values output by sensing elements of a chemical sensing unit, according to some embodiments of the technology described herein.

FIG. 6 illustrates a flowchart of an example process 600 of generating a set of features using measured values output by sensing elements of a chemical sensing unit, according to some embodiments of the technology described herein. Process 600 may be performed by chemical sensing system 110 described herein with reference to FIG. 1. For example, process 600 may be performed by event detection system 114 and/or inference system 116. In some embodiments, process 600 may be performed to generate a set of features at block 502 of process 500 described herein with reference to FIG. 5.

Process 600 begins at block 602, where the system receives measured values output by sensing elements (e.g., of chemical sensing unit 112). The system may be configured to receive the measured values output by the sensing elements as described at block 402 of process 400 described herein with reference to FIG. 4. The system may be configured to receive measured values output at points in a period of time (e.g., a time window). As an illustrative example, the system may receive a set of measured values $x_1, x_2, \ldots, x_m$ output by a set of m sensing elements at each timepoint. The measured values output at a timepoint may be used by the system to generate an m-dimensional vector $x=(x_1, x_2, \ldots, x_m)$.

Next, process 600 proceeds to block 604, where the system generates descriptors using the measured values. In some embodiments, the system may be configured to generate a descriptor for a timepoint by normalizing the measured output values. The system may be configured to normalize the set of measured values for each timepoint. Continuing with the example above, the system may generate a normalized vector $n=(n_1, n_2, \ldots, n_m)$ using a baseline vector $bl=(bl_1, bl_2, \ldots, bl_m)$ as shown in equation 1 below.

$$n_i = \left(\frac{x_i}{bl_i}\right) - 1, \text{ for } 1 \le i \le m \qquad \text{Eqution (1)}$$

In equation 1, $x_i$ indicates a measured output value of a respective sensing element, and $bl_i$ indicates a baseline value for the sensing element from baseline vector bl.

Next, process 600 proceeds to block 606, where the system generates a chronological descriptor using the descriptors generated at block 604. The system may be configured to generate a chronological descriptor by combining a sequence of descriptors generated from sets of measured values output over a period of time. For example, the system may generate a chronological descriptor $C=(n^t, n^{t+1}, \ldots, n^{t+s})$, for $s \ge 0$ and for $t \ge 1$, where each $n^t$ indicates a descriptor generated from measured values output at timepoint t. Each chronological descriptor may represent a respective window of time. In some embodiments, the window of time may overlap with a window of time represented by another chronological descriptor. For example, a first chronological descriptor may be generated using a first set of attributes, and a second chronological descriptor may be generated using a second set of attributes, where the first and second sets of descriptors share at least one, but not all, attributes. In some embodiments, the window of time may not overlap with a window of time represented by another chronological descriptor. For example, a first chronological descriptor may be generated using a first set of attributes, and a second chronological descriptor may be generated using a second set of attributes, where the first and second sets of attributes do not share any descriptors.

Next, process 600 proceeds to block 608, where the system generates a set of features using the chronological descriptors. In some embodiments, the system may be configured to generate the set of features using a single chronological descriptor (e.g., representing a window of time). For example, the system may generate a set of features to be the chronological descriptor. In some embodiments, the system may be configured to generate the set of features using multiple chronological descriptors (e.g., representing respective windows of time). For example, the system may determine the set of features to be concatenated chronological descriptors $C_1, \ldots, C_b$, for $b \geq 2$. In some embodiments, one or more chronological descriptors may represent an event. For example, the chronological descriptor(s) may be used to generate an inference for the event.

Figure 7:
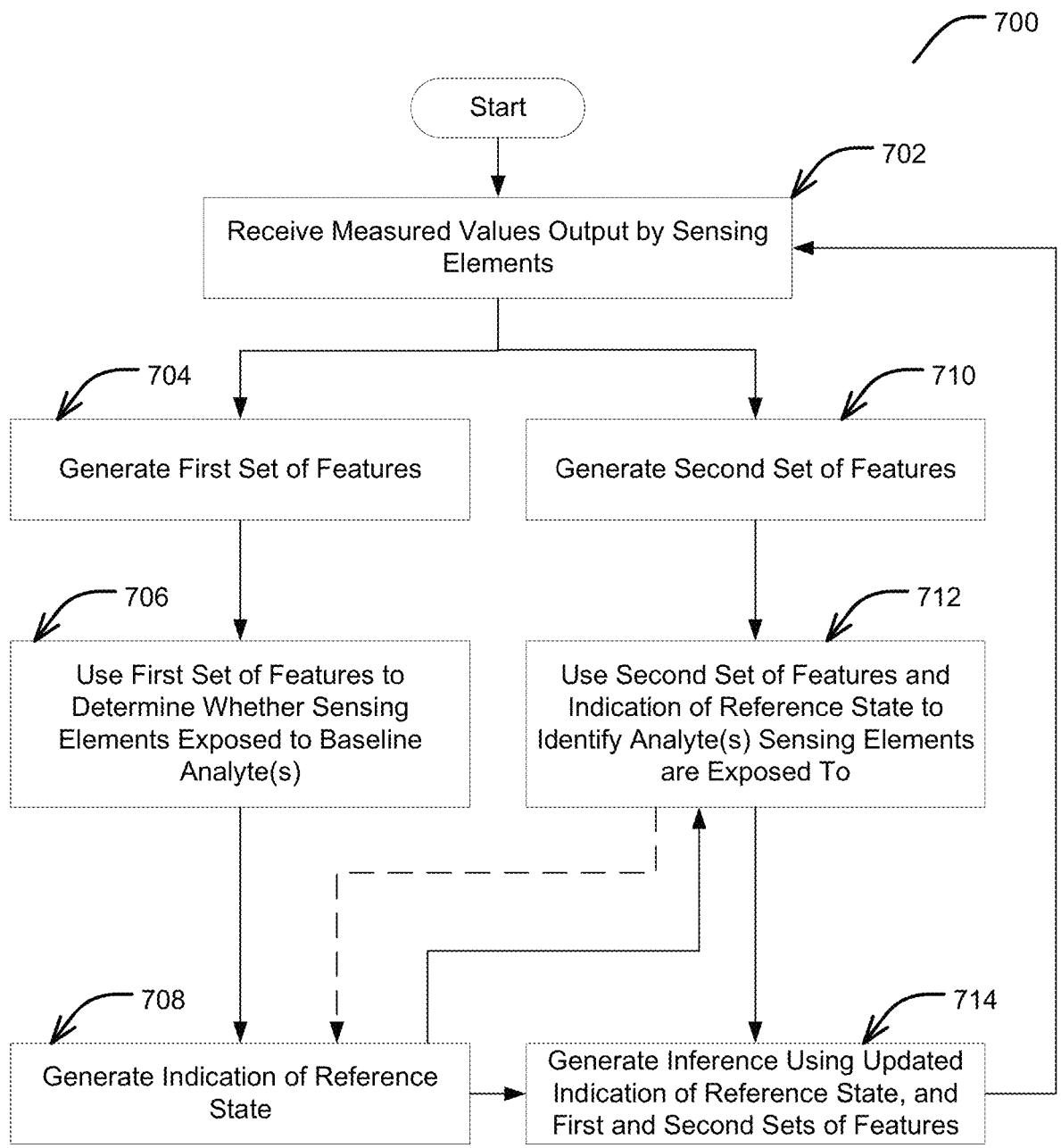
FIG. 7 illustrates a flowchart of an example process of generating an inference based on identification of an event, according to some embodiments of the technology described herein.

FIG. 7 illustrates a flowchart of an example process 700 of generating an inference based on identification of a change from a reference state, according to some embodiments of the technology described herein. Process 700 may be performed by chemical sensing system 110 described herein with reference to FIG. 1. In some embodiments, process 700 may be performed by event detection system 114 and inference system 116. In some embodiments, process 700 may be performed by component 320 described herein with reference to FIG. 3. In some embodiments, process 700 may be performed as part of process 400 described herein with reference to FIG. 4.

Process 700 begins at block 702, where the system receives measured values output by sensing elements. The system may be configured to receive the measured values output by the sensing elements as described at block 402 of process 400 described herein with reference to FIG. 4 and/or block 602 of process 600 described herein with reference to FIG. 6.

After receiving the measured values output by the sensing elements at block 702, the system may be configured to perform the steps at block 704-708 to generate an indication of a reference state. At block 704, the system generates a first set of features. The system may be configured to generate the first set of features as described herein with reference to FIG. 6. For example, the system may generate the first set of features representing an environment during a respective time window (e.g., represented by one or more chronological descriptors).

Next, process 700 proceeds to block 706, where the system uses the first set of features to determine whether sensing elements are exposed to one or more baseline analytes. The baseline analyte(s) may be analyte(s) expected outside of an event. For example, the baseline analyte(s) may be present in air in a kitchen when no cooking is being performed. In another example, the baseline analyte(s) may be present in air in a space when there is no spoiled food in the space. In some embodiments, the system may be configured to determine whether the sensing elements are exposed to the baseline analyte(s) by providing the first set of features as input to a machine learning model to obtain an output. For example, the machine learning model may be a neural network (e.g., a CNN, RNN, LSTM, or other type of neural network) that is trained to generate an output. The system may be configured to determine whether the sensing elements are exposed to the baseline analyte(s) based on the output. For example, the system may determine whether the output matches a predetermined indication of a reference state. In another example, the output of the machine learning model may indicate whether the sensing elements are exposed to the baseline analyte(s).

After receiving the measured values output by the sensing elements at block 702, the system performs steps at blocks 710-714 to generate an inference. At block 710, the system generates a second set of features. The system may generate the second set of features as described herein with reference to FIG. 6. The second set of features may represent one or more analytes sensed by the sensing elements during a period of time.

Next, process 700 proceeds to block 708, where the system generates an indication of a reference state. In some embodiments, the system may be configured to generate the indication of the reference state based on whether the sensing elements are exposed to the baseline analyte(s). In some embodiments, the system may be configured to generate an indication of the reference state using a machine learning model. For example, the system may obtain a latent representation of a machine learning model generated using the first set of features as the indication of the reference state. In some embodiments, the system may be configured to generate the indication of the reference state when it is determined that the sensing elements are exposed to the baseline analyte(s). As an illustrative example, the latent representation may be values output by a layer of a neural network (e.g., a CNN or RNN).

In some embodiments, the system may be configured to generate the indication of the reference state by updating a previous indication of the reference state. For example, the system may determine that a reference state is represented by a different set of baseline analyte(s). The system may thus update the indication of the reference state based on the baseline analyte(s). In some embodiments, the system may be configured to update the indication of the reference state by: (1) generating a set of features using measurements obtained from exposure to analyte(s) of the reference state; and (20 providing the set of features as input to a machine learning model to obtain an output (e.g., a latent representation). The system may be configured to use the output as the updated indication of the reference state.

Next, process 700 proceeds to block 712, where the system uses the second set of features and a current indication of the reference state to identify one or more analytes that the sensing elements are exposed to. In some embodiments, the system may be configured to provide the second set of features and the indication of the reference state as input to a machine learning model to obtain output indicating the analyte(s). For example, the system may provide the second set of features and the reference state as input to a neural network (e.g., an RNN, CNN, or other type of neural network) to obtain output indicating the analyte(s). In some embodiments, the output may be a classification generated by the machine learning model indicating the analyte(s).

As indicated by the dotted line from block 712 to 708, in some embodiments, the system may be configured to update the indication of the reference state based on an identification of one or more analytes that the sensing elements are determined to be exposed to. For example, the system may determine that the current analyte(s) that the sensing elements are exposed to are baseline analyte(s) (e.g., from performing process 706). The system may update the indication of the reference state based on the determination. For example, the system may use the first and/or second set of features to obtain an updated latent representation of a machine learning model as the updated indication of the reference state.

Next, process 700 proceeds to block 714, where the system generates an inference using the updated indication of the reference state, and the first and second sets of features. In some embodiments, the system may be configured to use the indication of the reference state and the first and second sets of features to generate input to a machine learning model (e.g., a neural network) to generate an inference. For example, the system may use the indication of the reference state as a first portion of an input layer of a neural network, and the first and second sets of features representing the analyte(s) that the sensing elements are presently exposed to as a second portion of an input layer of the neural network. The neural network may generate an output inference based on the input. For example, the output inference may indicate a concentration of chemical(s) in the environment, a scent present in the environment, or a stage of cooking a recipe.

In some embodiments, the system may be configured to continuously generate an inference using the indication of the reference state (e.g., at every iteration of providing an input to a machine learning model). By incorporating the indication of the reference state in generating the inference, the system may: (1) identify a change from the reference state indicative of an event; and (2) generate an inference for the event. After generating the inference at block 714, process 700 may return to block 702, where the system receives a new set of measured values output by the sensing elements. The system may use the new measured values to update the indication of the reference state.

Although the example of FIG. 7 shows generation of first and second sets of features, in some embodiments, the system may generate one set of features that are used as both the first and second set of features as described herein in process 700. For example, the set of features may represent a current set of analyte(s) that the sensing elements are exposed to.

Figure 10:
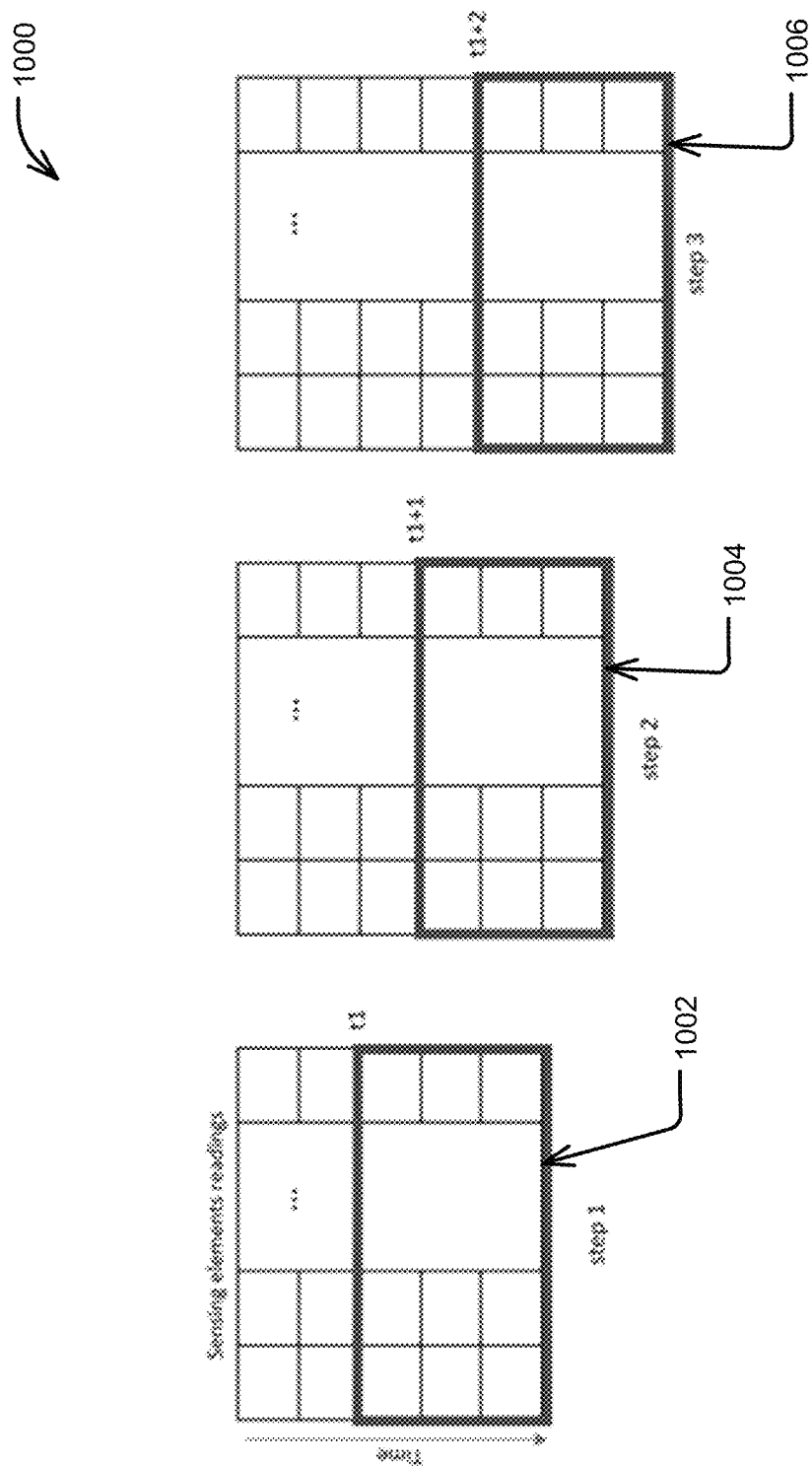
FIG. 10, illustrates a diagram illustrating reading of measured values output by sensing elements of a chemical sensing unit over time, according to some embodiments of the technology described herein.

FIG. 10, illustrates a diagram 1000 illustrating reading of measured values output by sensing elements of a chemical sensing unit over time, according to some embodiments of the technology described herein. Each of the steps shown in the diagram 1000 may represent a set of measured values received by the system performing process 1000 at a respective iteration of the process 1000. The first step 1002 indicates measured output values obtained at a time t1, the second step 1004 indicates measured output values obtained at a subsequent time (t1+1), and the third step 1006 indicates measured output values obtained at a subsequent time (t1+ 2). The system thus periodically updates an indication of a reference state based on updates in measured values output by sensing elements over time. As shown in FIG. 10, in some embodiments, the time windows at different steps may overlap. In some embodiments, the time windows may not overlap. For example, none of the measured values received in one iteration may be included in measured values received at a subsequent iteration.

Figure 8:
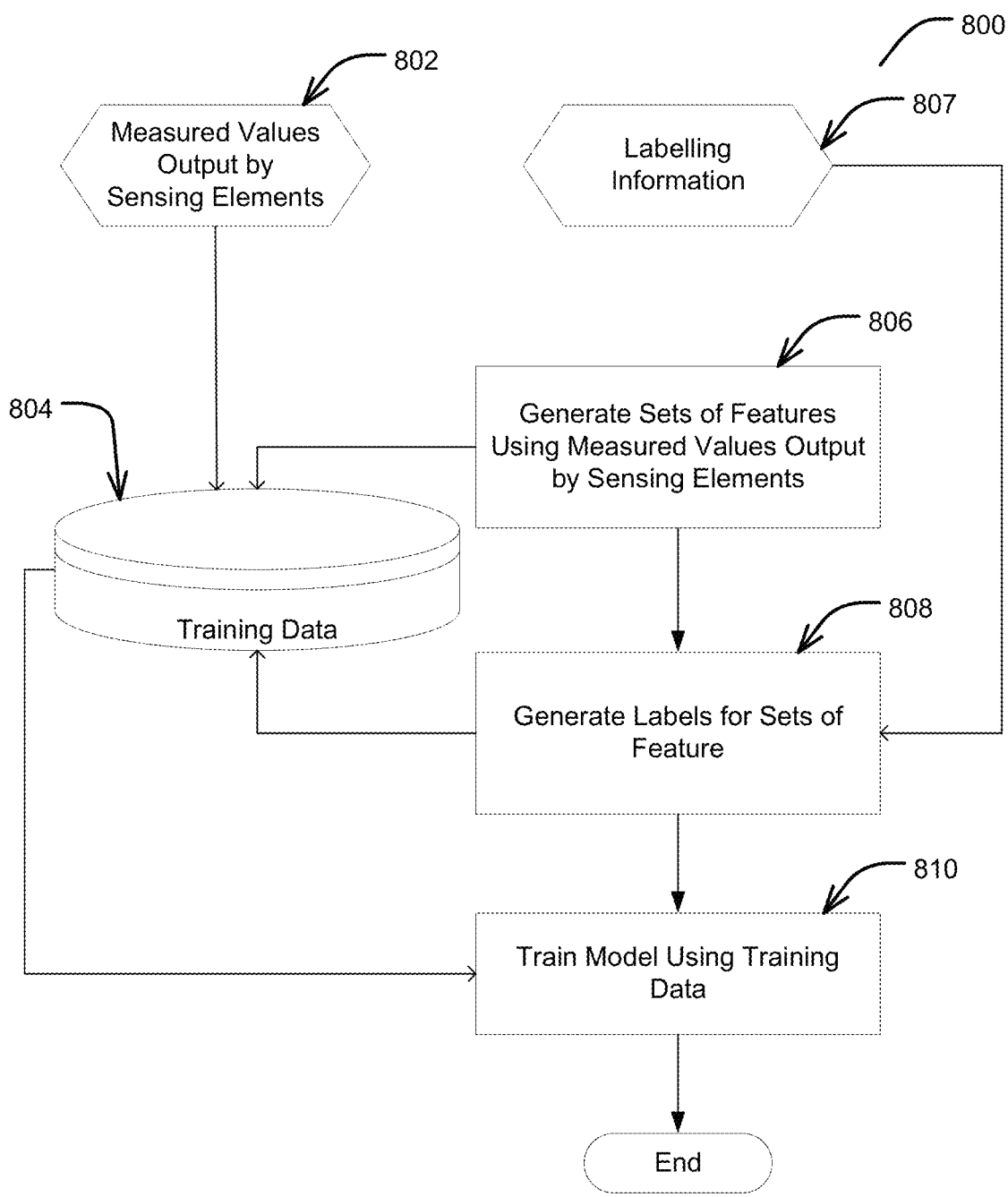
FIG. 8 illustrates a flowchart of an example process of training a machine learning model, according to some embodiments of the technology described herein.

FIG. 8 illustrates a flowchart of an example process 800 of training a machine learning model, according to some embodiments of the technology described herein. Process 800 may be performed by any suitable computing device. In some embodiments, process 800 may be performed to train a machine learning model for detection of an event (e.g., to recognize pattern(s) indicative of the event). In some embodiments, process 800 may be performed to train a machine learning model for generation of an indication of a reference state. In some embodiments, process 800 may be performed to train a machine learning model for generating an inference about chemical characteristic(s) of an environment.

In some embodiments, the machine learning model may be a neural network. For example, the machine learning model may be a CNN, RNN, LSTM, or other type of neural network. In some embodiments, the machine learning model may be a support vector machine (SVM), a logistic regression model, a decision tree model, or any other suitable machine learning model. Process 800 may be performed to learn parameters of the machine learning model. For example, process 800 may be performed to learn weights of a neural network.

Process 800 begins with the system performing process 800 receiving measured values (e.g., voltage signal values) output by sensing elements (e.g., of chemical sensing system 110 described herein with reference to FIG. 1). The system stores the measured values output by the sensing elements in data storage 804 for use in training the machine learning model. In some embodiments, the data storage 804 may be memory of the system performing process 800. For example, the data storage may be a hard drive of the system. In some embodiments, the data storage 804 may be data storage separate from the system. For example, the data storage 804 may be a remote database, an external hard drive, or a cloud based storage system.

Next, process 800 proceeds to block 806, where the system generates sets of features using the measured values output by the sensing elements stored in data storage 804. The system may be configured to generate the sets of features as described in process 600 described herein with reference to FIG. 6. In some embodiments, each of the sets of features may represent a time period of exposure of the sensing elements to one or more analytes (e.g., analytes 102) in an environment of a chemical sensing system. For example, each of the sets of features may represent a time period of 5 seconds, 30 seconds, 1 minute, 5 minutes, 10 minutes, 30 minutes, 1 hour, 2 hours, 4 hours, 6 hours, 8 hours, 12 hours, 24 hours, or other suitable time period. The system may be configured to store the generated sets of features in a data storage 804.

Next, process 800 proceeds to block 808, where the system generates labels for the sets of features. In some embodiments, the system may be configured to generate a label for each set of features indicative of whether the set of features corresponds to an event. For example, the system may label each set of features with a binary value, where a value of 1 indicates that the set of features corresponds to an event and a value of 0 indicates that the set of features does not correspond to an event. In some embodiments, the system may be configured to label sets of features corresponding to an event with a label indicating a type of event. For example, the system may label the set of features with classifications of types of events that the sets of features correspond to. As an illustrative example, the system may label each of the sets of features that correspond to an event with a respective stage of cooking a recipe. In some embodiments, the system may be configured to generate a label for each set of features indicative of whether the set of features corresponds to a reference state of an environment. For example, the system may label each set of features with a binary value, where a value of 1 indicates that the set of features corresponds to a reference state and a value of 0 indicates that the set of features does not correspond to a reference state. As shown in FIG. 8, the system may be configured to store the generated labels in the data storage 804.

As shown in FIG. 8, in some embodiments, the system may be configured to generate the labels using labelling information 807. In some embodiments, the labelling information may include an indication of labels input by a user. In some embodiments, the labelling information may include an indication of labels generated by another system. For example, the labelling information may include information generated by one or more sensors. In another example, the labelling information may include images captured by a camera. The system may be configured to use the labelling information to generate labels for the sets of features. For example, the system may assign a label to each set of features based on a user indication of whether the set of features corresponds to occurrence of an event and/or an indication from another system indicating whether the set of features corresponds to occurrence of an event.

Next, process 800 proceeds to block 810, where the system trains the machine learning model using the training data (e.g., sets of features and corresponding labels) stored in the data storage 804. In some embodiments, the system may be configured to train the machine learning model by applying a supervised learning technique to the training data. In some embodiments, the system may be configured to perform an iterative training technique. For example, the system may perform stochastic gradient descent to train the machine learning model (e.g., to learn parameters of the machine learning model). In this example, the system may: (1) provide sets of features as input to a machine learning model to obtain respective outputs (e.g., classifications); (2) determining a measure of difference between the outputs to the labels representing the target output of the machine learning model for the sets of features provided as input; and (3) updating parameters of the machine learning model based on the measure of difference. The system may be configured to perform multiple iterations of steps (1) to (3) to learn parameters of the machine learning model. For example, the system may iterate until the measure of difference meets a threshold and/or until a threshold number of iterations have been performed. In some embodiments, the system may be configured to use a loss function as the measure of difference. For example, the system may use a mean squared error (MSE) loss function, a mean absolute error (MAE) loss function, a binary cross-entry loss function, Kullback-Leibler Divergence loss function, or other suitable loss function.

After training the machine learning model, the machine learning model may be used (e.g., by chemical sensing system 110). For example, the machine learning model may be used to detect occurrence of an event in an environment (e.g., environment 100). In another example, the machine learning model may be used to generate an indication of a reference state. In another example, the machine learning model may be used to generate an inference about the environment (e.g., chemical characteristic(s) of the environment).

Figure 11:
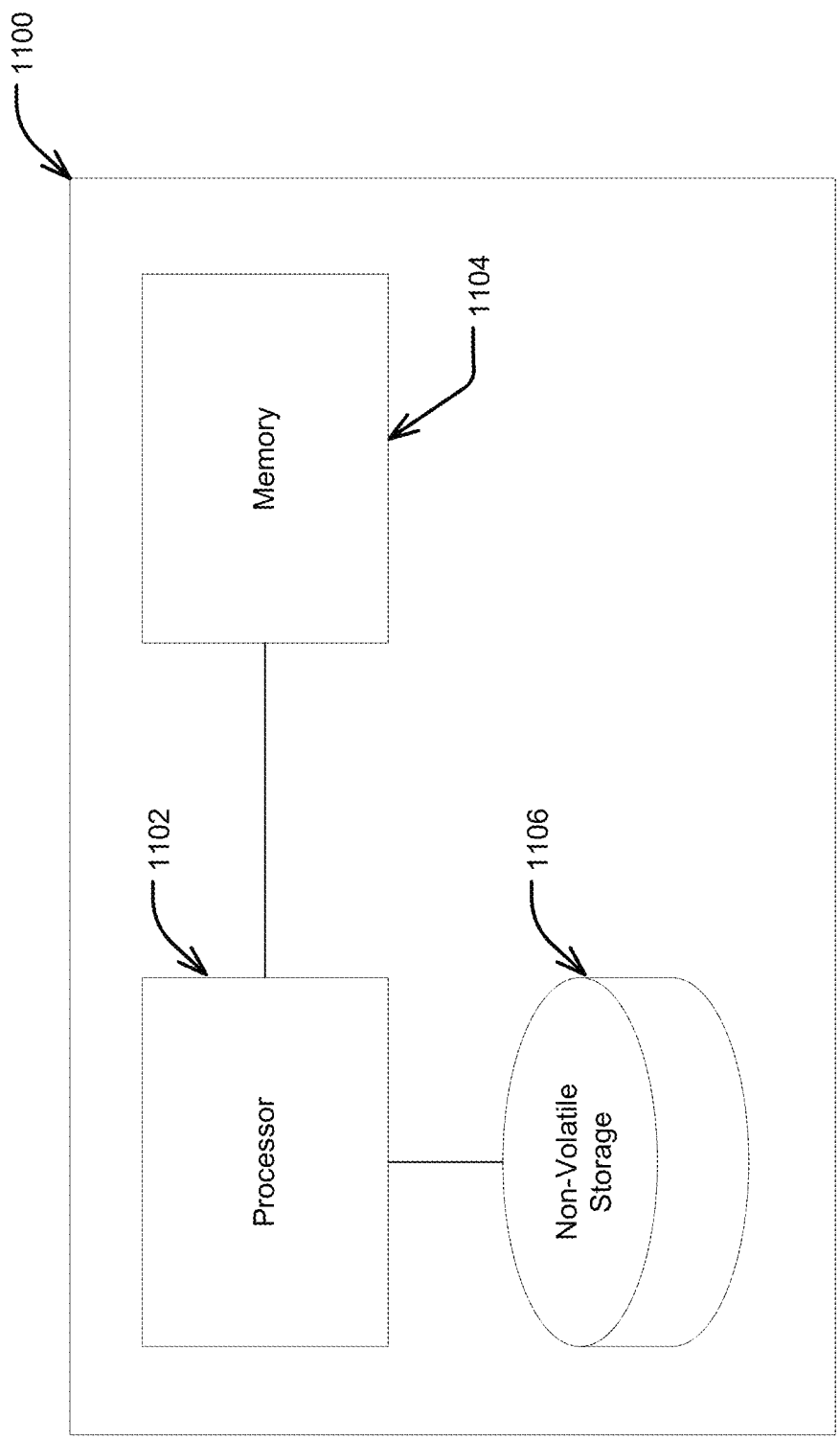
FIG. 11 depicts an illustrative implementation of a computer system that may be used in connection with some embodiments of the technology described herein.

FIG. 11 shows a block diagram of an example computer system 1100 that may be used to implement embodiments of the technology described herein. The computing device 1100 may include one or more computer hardware processors 1102 and non-transitory computer-readable storage media (e.g., memory 1104 and one or more non-volatile storage devices 1106). The processor(s) 1102 may control writing data to and reading data from (1) the memory 1104; and (2) the non-volatile storage device(s) 1106. To perform any of the functionality described herein, the processor(s) 1102 may execute one or more processor-executable instructions stored in one or more non-transitory computer-readable storage media (e.g., the memory 1104), which may serve as non-transitory computer-readable storage media storing processor-executable instructions for execution by the processor(s) 1102.

The terms "program" or "software" are used herein in a generic sense to refer to any type of computer code or set of processor-executable instructions that can be employed to program a computer or other processor (physical or virtual) to implement various aspects of embodiments as discussed above. Additionally, according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform tasks or implement abstract data types. Typically, the functionality of the program modules may be combined or distributed.

The above-described embodiments can be implemented in any of numerous ways. For example, the embodiments may be implemented using hardware, software, or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein comprises at least one computer-readable storage medium (e.g., RAM, ROM, EEPROM, flash memory or other memory technology, CD-ROM, digital versatile disks (DVD) or other optical disk storage, magnetic cassettes, magnetic tape, magnetic disk storage or other magnetic storage devices, or other tangible, non-transitory computer-readable storage medium) encoded with a computer program (i.e., a plurality of executable instructions) that, when executed on one or more processors, performs the above-discussed functions of one or more embodiments. The computer-readable medium may be transportable such that the program stored thereon can be loaded onto any computing device to implement aspects of the techniques discussed herein. In addition, it should be appreciated that the reference to a computer program which, when executed, performs any of the above-discussed functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques discussed herein.

The foregoing description of implementations provides illustration and description, but is not intended to be exhaustive or to limit the implementations to the precise form disclosed. Modifications and variations are possible in light of the above teachings or may be acquired from practice of the implementations. In other implementations the methods depicted in these figures may include fewer operations, different operations, differently ordered operations, and/or additional operations. Further, non-dependent blocks may be performed in parallel.

It will be apparent that example aspects, as described above, may be implemented in many different forms of software, firmware, and hardware in the implementations illustrated in the figures. Further, certain portions of the implementations may be implemented as a "module" that performs one or more functions. This module may include hardware, such as a processor, an application-specific integrated circuit (ASIC), or a field-programmable gate array (FPGA), or a combination of hardware and software.

What is claimed is:

1. A chemical sensing system comprising:
   a chemical sensing unit comprising a plurality of sensing elements, each of the plurality of sensing elements being configured to sense a respective one or more chemicals in an environment of the chemical sensing system;
   a computer processor; and
   a non-transitory computer-readable storage medium storing instructions that, when executed by the computer processor, cause the computer processor to perform a method comprising:
      receiving, from the chemical sensing unit, a first plurality of measurements comprising measured values output by the plurality of sensing elements at a plurality of points in a period of time;
      identifying, using the first plurality of measurements, a first timepoint corresponding to an occurrence of an event at least in part by analyzing the measured values output by the plurality of sensing elements to identify a pattern indicative of the occurrence of the event; and
      after identifying the occurrence of the event, generating an inference about one or more chemical characteristics of the environment of the chemical sensing system using a second plurality of measurements, the second plurality of measurements comprising measured values output by the plurality of sensing elements after the first timepoint.

2. The chemical system of claim 1, wherein analyzing the measured values output by the plurality of sensing elements to identify a pattern indicative of the occurrence of the event comprises determining that the measured values output by the plurality of sensing elements meet a predetermined pattern indicative of the occurrence of the event.

3. The chemical system of claim 1, wherein analyzing the measured values output by the plurality of sensing elements to identify the pattern indicative of the occurrence of the event comprises:
   generating a first set of features using at least one of the first plurality of measurements obtained at the first timepoint; and
   providing the first set of features as input to a machine learning model to obtain output indicating that the first timepoint corresponds to the occurrence of the event.

4. The chemical system of claim 1, wherein generating the inference about the one or more chemical characteristics of the environment using the second plurality of measurements comprises:
   generating a set of features using the second plurality of measurements; and
   providing the set of features as input to a machine learning model to obtain an output representing the inference about the one or more chemical characteristics of the environment.

5. The chemical system of claim 1, wherein the method comprises determining a reference state of the environment, wherein the reference state represents measured values output by the plurality of sensing elements outside of the event.

6. The chemical system of claim 5, wherein generating the inference about the one or more chemical characteristics of the environment comprises generating the inference using the second plurality of measurements and the reference state.

7. The chemical system of claim 6, wherein generating the inference using the second plurality of measurements and the reference state comprises:
   generating a set of features using the second plurality of measurements and the reference state; and
   providing the set of features as input to a machine learning model to obtain an output representing the inference about the one or more chemical characteristics of the environment.

8. The chemical system of claim 5, wherein analyzing the measured values output by the plurality of sensing elements to identify the pattern indicative of the occurrence of the event comprises identifying a change from the reference state indicative of the occurrence of the event.

9. The chemical system of claim 1, wherein the method further comprises outputting an indication of an action to be performed by a user based on the generated inference about the one or more chemical characteristics of the environment.

10. The chemical system of claim 1, wherein the method further comprises determining that an odor is present in the environment based on the inference about the one or more chemical characteristics of the environment.

11. The chemical system of claim 1, wherein generating the inference about the one or more chemical characteristics of the environment comprises determining a concentration of at least one chemical in the environment.

12. The chemical system of claim 1, wherein the second plurality of measurements comprises measured values output by the plurality of sensing elements before the first timepoint.

13. A method performed by a chemical sensing system to determine information about an environment of the chemical sensing system, the method comprising:
   sensing, by a plurality of sensing elements of a chemical sensing unit, one or more chemicals in the environment;
   using a computer processor to perform:
      receiving, from the chemical sensing unit, a first plurality of measurements comprising measured values output by the plurality of sensing elements at a plurality of points in time;
      identifying, using the first plurality of measurements, a first timepoint corresponding to an occurrence of an event at least in part by analyzing the measured values output by the plurality of sensing elements to identify a pattern indicative of the occurrence of the event; and after identifying the occurrence of the event, generating an inference about one or more chemical characteristics of the environment of the chemical sensing system using a second plurality of measurements, the second plurality of measurements comprising measured values output by the plurality of sensing elements after the first timepoint.

14. The method of claim 13, analyzing the measured values output by the plurality of sensing elements to identify the pattern indicative of the occurrence of the event comprises:
generating a first set of features using at least one of the first plurality of measurements obtained at the first timepoint; and
providing the first set of features as input to a machine learning model to obtain output indicating that the first timepoint corresponds to the occurrence of the event.

15. The method of claim 13, wherein generating the inference about the one or more chemical characteristics of the environment using the second plurality of measurements comprises:
generating a set of features using the second plurality of measurements; and
providing the set of features as input to a machine learning model to obtain an output representing the inference about the environment.

16. The method of claim 13, further comprising determining a reference state of the environment, wherein the reference state represents measured values output by the plurality of sensing elements outside of the event.

17. The method of claim 16, wherein generating the inference about the one or more chemical characteristics of the environment comprises generating the inference using the second plurality of measurements and the reference state.

18. The method of claim 17, wherein generating the inference using the second plurality of measurements and the reference state comprises:
generating a set of features using the second plurality of measurements and the reference state; and
providing the set of features as input to a machine learning model to obtain an output representing the inference about the one or more chemical characteristics of the environment.

19. The method of claim 16, wherein analyzing the measured values output by the plurality of sensing elements to identify the pattern indicative of the occurrence of the event comprises identifying a change from the reference state indicative of the occurrence of the event.

20. The method of claim 13, wherein generating the inference about the one or more chemical characteristics of the environment comprises determining a concentration of at least one chemical in the environment.

21. A system for determining information about an environment using measurement information obtained by a chemical sensing unit comprising a plurality of sensing elements, the system comprising:
a computer processor; and
a non-transitory computer-readable storage medium storing instructions that, when executed by the computer processor, cause the computer processor to perform a method comprising:
receiving, from the chemical sensing unit, a first plurality of measurements comprising measured values output by the plurality of sensing elements at a plurality of points in a period of time;
identifying, using the first plurality of measurements, a first timepoint corresponding to an occurrence of an event at least in part by analyzing the measured values output by the plurality of sensing elements to identify a pattern indicative of the occurrence of the event; and
after identifying the occurrence of the event, generating an inference about one or more chemical characteristics of the environment of the chemical sensing system using a second plurality of measurements, the second plurality of measurements comprising measured values output by the plurality of sensing elements after the first timepoint.

* * * * *